(12) United States Patent
Abaffy et al.

(10) Patent No.: US 12,186,294 B2
(45) Date of Patent: Jan. 7, 2025

(54) MODULATORS OF PROSTATE-SPECIFIC G-PROTEIN RECEPTOR (PSGR/OR51E2) AND METHODS OF USING SAME

(71) Applicant: Duke University, Durham, NC (US)

(72) Inventors: Tatjana Abaffy, Durham, NC (US); Hiro Matsunami, Durham, NC (US)

(73) Assignee: Duke University, Durham, NC (US)

( * ) Notice: Subject to any disclaimer, the term of this patent is extended or adjusted under 35 U.S.C. 154(b) by 360 days.

(21) Appl. No.: 16/780,604

(22) Filed: Feb. 3, 2020

(65) Prior Publication Data

US 2020/0253912 A1 Aug. 13, 2020

Related U.S. Application Data

(62) Division of application No. 15/801,258, filed on Nov. 1, 2017, now Pat. No. 10,588,884.

(60) Provisional application No. 62/415,591, filed on Nov. 1, 2016.

(51) Int. Cl.

| A61K 31/203 | (2006.01) |
| A61K 31/19 | (2006.01) |
| A61K 31/352 | (2006.01) |
| A61K 31/565 | (2006.01) |
| A61K 31/568 | (2006.01) |
| A61K 31/7016 | (2006.01) |
| A61K 47/06 | (2006.01) |

(52) U.S. Cl.
CPC ............ *A61K 31/203* (2013.01); *A61K 31/19* (2013.01); *A61K 31/352* (2013.01); *A61K 31/565* (2013.01); *A61K 31/568* (2013.01); *A61K 31/7016* (2013.01); *A61K 47/06* (2013.01)

(58) Field of Classification Search
None
See application file for complete search history.

(56) References Cited

U.S. PATENT DOCUMENTS

| 2009/0075284 | A1* | 3/2009 | Chinnaiyan | ...... G01N 33/57434 435/6.12 |
| 2010/0292331 | A1* | 11/2010 | Mitchell | .......... G01N 33/57434 435/7.1 |
| 2010/0298270 | A1 | 11/2010 | Keana et al. | |

OTHER PUBLICATIONS

Cao et al. BMC Cancer, 2015, 15:915, 9 pages (Year: 2015).*
Maßberg et al. Oncotarget, 2016, vol. 7, No. 30, pp. 48231-48249 (Year: 2016).*
Marberger et al. British Medical Journal, Mar. 24, 1962, pp. 835-836 (Year: 1962).*
Song et al. Amino Acids, 2012, vol. 42, pp. 1897-1902 (Year: 2012).*
Struck-Lewicka et al. Journal of Pharmaceutical and Biomedical Analysis, 2015, vol. 111, pp. 351-361 (Year: 2015).*
Neuhaus et al., "Activation of an olfactory receptor inhibits proliferation of prostate cancer cells", Journal of Biological Chemistry, 284(24):16218-25 (Jun. 2009). Epub Apr. 2009.
Zhuang et al., "Evaluating cell-surface expression and measuring activation of mammalian odorant receptors in heterologous cells", Nature Protocols, 3(9):1402-13 (2008).
Xu et al., "PSGR, a novel prostate-specific gene with homology to a G protein-coupled receptor, is overexpressed in prostate cancer", Cancer Research, 60(23):6568-72 (Dec. 2000).
Luciferase Reporters, ThermoFisher Scientific, [retrieved on Apr. 2, 2018] [retrieved from the internet http://www.thermofisher.com/us/en/home/life-science/protein-biology/protein-biology-learning-center/protein-biology-resource-library/pierce-protein-methods/luciferase-reporters.html] [8 pages].
Dipaola et al., "A randomized phase II trial of mitoxantrone, estramustine and vinorelbine or bcl-2 modulation with 13-cis retinoic acid, interferon and paclitaxel in patients with metastatic castrate-resistant prostate cancer: ECOG 3899," J. Transl Med., 8:20 (Feb. 2010) [9 pages].
Abaffy et al., "A Testosterone Metabolite 19-Hydroxyandrostenedione Induces Neuroendocrine Trans-Differentiation of Prostate Cancer Cells via an Ectopic Olfactory Receptor," Front. Oncol., 8:162 (May 2018) [15 pages].
Dahiya et al., "Inhibition of tumorigenic potential and prostate-specific antigen expression in LNCaP human prostate cancer cell line by 13-cis-retinoic acid," Int J. Cancer, 59(1):126-32 (Oct. 1994).
Schäfer et al., "Failure is an option: learning from unsuccessful proof-of-concept trial," Drug Discov Today, 13 (21-22):913-6 (Nov. 2008) Epub Jun. 2008.
Horig et al., "From bench to clinic and back: Perspective on the 1st IQPC Translational Research conference," J. Transl Med., 2(1):44 (Dec. 2004).
Johnson et al., "Metabolomics: beyond biomarkers and towards mechanisms," Nat Rev Mol Cell Biol. (Jul. 2016); 17(7):451-459.

* cited by examiner

*Primary Examiner* — James D. Anderson
(74) *Attorney, Agent, or Firm* — POLSINELLI PC

(57) ABSTRACT

The present disclosure provides, in part, modulators of prostate-specific G-protein receptor (OR51E2/PSGR) and methods of treating, preventing, and diagnosing prostate cancer using the same.

6 Claims, 33 Drawing Sheets

MODULATORS OF PROSTATE-SPECIFIC G-PROTEIN RECEPTOR (PSGR/OR51E2) AND METHODS OF USING SAME

CROSS-REFERENCE TO RELATED APPLICATIONS

This application is a divisional of U.S. application Ser. No. 15/801,258, filed on Nov. 1, 2017, which claims the benefit of priority of U.S. Provisional Patent Application No. 62/415,591, filed on Nov. 1, 2016, the entire contents of each of which are hereby incorporated by reference.

FEDERAL FUNDING LEGEND

The work described herein was funded, in whole or in part, using funds from the Federal Government under NIH Grant No.: R01 DC124423. Consequently, the Federal Government has certain rights to this invention.

BACKGROUND

Prostate cancer is the second most common cancer in men, accounting for 70% of all cancer cases in the developed world. Most deaths from prostate cancer are due to the progression of localized disease into metastatic, castration-resistant prostate cancer (CRPC). Androgen deprivation therapy is an established treatment for advanced prostate cancer. However, many men eventually fail this therapy and die of CRPC. Recent research attributes the progression of CRPC to neuroendocrine trans-differentiation (NEtD) of cancerous prostate cells. However, the mechanism through which NEtD occurs in prostate cancer remains unclear. Clinical observations have suggested that NEtD correlates with cancer progression and poor prognosis.

The presence of olfactory receptor OR51E2, also known as Prostate Specific G-protein Receptor (PSGR), in prostate cancer is well documented, but its function is not completely understood. This G protein-coupled receptor (GPCR) is expressed in healthy prostate tissue and is significantly over-expressed in prostate cancer. Furthermore, increased expression of OR51E2/PSGR in CRPC has been documented, but its role and function in disease progression is currently unknown. Xu et al. demonstrated an increased abundance of OR51E2 in LNCaP cells during androgen deprivation. Androgen deprivation results in G0-G1 arrest, cellular senescence, an NE cell-like phenotype, and development of highly aggressive clones. (Xu et al. (2000) *Cancer Research* 60:6568-72).

Furthermore, epidemiological, histopathological, and genetic studies have shown that chronic infection and inflammation are important in prostate carcinogenesis. Many agents can induce inflammation of the prostate. One such agent is *Propionibacterium acnes*, which is predominantly a skin commensal bacterium, but is also found in the oral cavity and gastrointestinal tract. *P. acnes* is involved in the pathogenesis of acne and is often recognized as an opportunistic pathogen and the cause of chronic post-operative prosthetic joint infections, osteomyelitis, and endocarditis. *P. acnes* infection induces a strong inflammatory response and IL-6, IL-8, and GM-CSF secretion. *P. acnes* produce propionic acid (PA), which causes acute and chronic prostatitis. Chronic infection produces a constant supply of PA, which acts as an agonist for OR51E2. Short-term activation of OR51E2 in prostate epithelial cells (RWPE-2) causes an inflammatory reaction, while prolonged/chronic activation may facilitate NEtD, thus contributing to a more aggressive phenotype.

Currently identified agonists for OR51E2 include propionic acid, acetic acid, androstenone derivatives, and beta-ionone. The only known antagonist is alpha-ionone, an aroma compound. However, it is unknown whether any of these ligands have an active role in prostate cancer pathogenesis.

The incidence of prostate cancer is increasing worldwide and there is an urgent need for better diagnostic strategies to distinguish between indolent and aggressive tumors, and to develop more efficacious treatment options for highly aggressive tumors. The results described herein demonstrate that chronic agonist-mediated activation of the OR51E2/PSGR receptor can turn this receptor into an oncogene and thereby facilitate cellular progression and transformation resulting in NEtD, a characteristic phenotype of CRCP. Additionally, the ligands described herein represent potential novel anti-cancer and diagnostic agents. Results from the studies of the present invention assist in defining the role and function of OR51E2/PSGR. In particular, the identification of novel metabolite-agonists provides important molecular and biochemical insights into the biological role of this receptor in prostate tissue physiology and pathophysiology. Finally, the inducement of NEtD by prolonged activation of OR51E2 by PA, a product of *P. acnes* fermentation, elucidates a causal link between chronic inflammation and NED in prostate cancer.

BRIEF SUMMARY OF THE INVENTION

The present disclosure is based, in part, on the finding that modulation of the OR51E2 receptor results in significant phenotypic changes indicative of neuroendocrine phenotypes, which are resistant to current treatments. These results demonstrate that the OR51E2/PSGR receptor is a valid therapeutic target for treating, preventing, and diagnosing castrate-resistant prostate cancer (CRPC).

One aspect of the present disclosure provides a method of treating prostate cancer or preventing the progression of prostate cancer in a subject in need thereof, comprising: administering to a subject a therapeutically effective amount of one or more OR51E2 ligands, wherein the ligand binds to OR51E2 on a prostate cancer cell and impedes the progression of the prostate cancer cell.

In some embodiments of the above aspect of the invention, the OR51E2 ligand is an OR51E2 agonist and/or an OR51E2 antagonist. In other embodiments, the OR51E2 ligand is estriol, epitestosterone, 19-OH AD (19-hydroxy-androst-4-ene-3,17-dione), palmitic acid, androstenedione, D-alanyl-d-alanine, glycylglycine, kojibiose, urea, AFMK (N-acetyl-N-formyl-5-metoxykynurenamine), pelargonidin, hydroxypyruvic acid, adenosine 2',3'-cyclic phosphate, gamma-CEHC, tetrahydrocurcumin, N-acetylglutamic acid, L-histidinol, bradykinin, 8-Hydroxyguanine, imidazolone, 2-pyrrolidinone, 2-ketoglutaric acid, L-glyceric acid, glycine, propionic acid, or 13-cis retinoic acid.

In some embodiments of the above aspects of the invention, the prostate cancer cell is a castrate resistant prostate cancer cell.

In some embodiments of the above aspects of the invention, the subject suffers from chronic infection or inflammation. In other embodiments, the subject suffers from a *P. acnes* infection.

Another aspect of the present disclosure provides a method of impeding the progression of a prostate cancer cell, comprising contacting the prostate cancer cell with one or more OR51E2 ligands.

In some embodiments of the above aspects of the invention, the OR51E2 ligand is an OR51E2 agonist and/or an OR51E2 antagonist. In other embodiments, the OR51E2 ligand is estriol, epitestosterone, 19-OH AD (19-hydroxy-androst-4-ene-3,17-dione), palmitic acid, androstenedione, D-Alanyl-d-alanine, glycylglycine, kojibiose, urea, AFMK (N-acetyl-N-formyl-5-metoxykynurenamine), pelargonidin, hydroxypyruvic acid, adenosine 2',3'-cyclic phosphate, gamma-CEHC, tetrahydrocurcumin, N-acetylglutamic acid, L-histidinol, bradykinin, 8-hydroxyguanine, imidazolone, 2-pyrrolidinone, 2-ketoglutaric acid, L-glyceric acid, glycine, propionic acid, or 13-cis retinoic acid.

In some embodiments of the above aspects of the invention, the prostate cancer cell is a castrate resistant prostate cancer cell.

Yet another aspect of the present disclosure provides a method of diagnosing prostate cancer in a subject, comprising: a) obtaining a biological sample from the subject; b) contacting the sample with one or more OR51E2 ligands; c) detecting an increase and/or decrease in the level of one or more metabolites associated with ligand-bound OR51E2 in the sample as compared to a sample not contacted with one or more OR51E2 ligands; and d) identifying the presence of prostate cancer based on the increase and/or decrease of said metabolites.

In some embodiments of the above aspect of the invention, the method of diagnosing prostate cancer in a subject comprises detecting a decrease in the level of lactic acid, serine, threonine, glucose-6 phosphate, fructose-6 phosphate, fumaric acid, glutamic acid, beta-alanine, ornithine, and inosine. In other embodiments, the method of diagnosing prostate cancer in a subject further comprises detecting an increase in the level of intracellular phosphoenolpyruvate and an increase in the level of extracellular levels of cystine, aparagine, glutaric acid, guanine, and glutamine.

In some embodiments of the above aspects of the invention, the OR51E2 ligand is an OR51E2 agonist and/or an OR51E2 antagonist. In other embodiments, the OR51E2 ligand is estriol, epitestosterone, 19-OH AD (19-hydroxy-androst-4-ene-3,17-dione), palmitic acid, androstenedione, D-Alanyl-d-alanine, glycylglycine, kojibiose, urea, AFMK (N-acetyl-N-formyl-5-metoxykynurenamine), pelargonidin, hydroxypyruvic acid, adenosine 2',3'-cyclic phosphate, gamma-CEHC, tetrahydrocurcumin, N-acetylglutamic acid, L-histidinol, bradykinin, 8-hydroxyguanine, imidazolone, 2-pyrrolidinone, 2-ketoglutaric acid, L-glyceric acid, glycine, propionic acid, or 13-cis retinoic acid.

In some embodiments of the above aspects of the invention, the presence of NEtD of prostate cancer cells is identified.

In some embodiments of the above aspects of the invention, the biological sample is a tissue sample, blood sample, serum sample, or urine sample.

BRIEF DESCRIPTION OF THE DRAWINGS

The foregoing aspects and other features of the invention are explained in the following description, taken in connection with the accompanying drawings, wherein:

FIG. 26A shows a microscope image of cells incubated in regular medium. FIG. 26B shows a microscope image of cells incubated in androgen-deprived medium (charcoal-dextran treated medium) for 5 days.

DETAILED DESCRIPTION OF THE INVENTION

Figure 1:
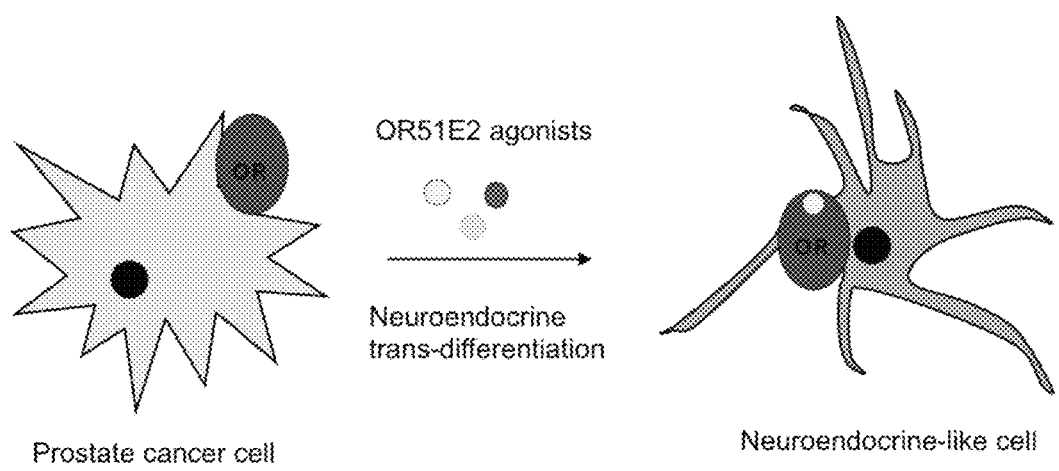
FIG. 1 is a schematic showing prostate epithelial cell differentiation to the NED phenotype.

For the purposes of promoting an understanding of the principles of the present disclosure, reference will now be made to embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

The terminology used herein is for the purpose of describing particular embodiments only and is not intended to be limiting of the invention.

Articles "a" and "an" are used herein to refer to one or to more than one (i.e. at least one) of the grammatical object of the article. By way of example, "an element" means at least one element and can include more than one element.

As used herein, the term "and/or" includes any and all combinations of one or more of the associated listed items. As used herein, the singular forms "a," "an," and "the" are intended to include the plural forms as well as the singular forms, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

Unless otherwise defined, all terms (including technical and scientific terms) used herein have the same meaning as commonly understood by one having ordinary skill in the art to which this disclosure belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

In describing the invention, it will be understood that a number of aspects and embodiments are disclosed. Each of these has individual benefit and each can also be used in conjunction with one or more, or in some cases all, of the other disclosed aspects and embodiments. Accordingly, for the sake of clarity, this description will refrain from repeating every possible combination of the individual aspects and embodiments in an unnecessary fashion. Nevertheless, the specification and claims should be read with the understanding that such combinations are implicitly discloses, and are entirely within the scope of the invention and the claims, unless otherwise specified.

The present disclosure is based, in part, on the finding that modulation of the olfactory receptor 51E2 (OR51E2), also known as the Prostate-Specific G-Protein Coupled Receptor (PSGR), results in significant phenotypic changes indicative of neuroendocrine phenotypes, which are resistant to current treatments.

The terms "OR51E2," "PSGR," and "OR51E2/PSGR" are used interchangeably to refer to the olfactory receptor 51E2 (OR51E2) receptor.

Neuroendocrine differentiation: Neuroendocrine (NE) cells are scattered through the epithelium compartment of normal human prostate. NE cells are typically responsible for growth, differentiation, and secretory activity of the prostatic epithelium. As prostate cancer advances, epithelial cells throughout the prostate epithelium differentiate into neuroendocrine-like (NE-like) cells. NE-like cells contain dendritic cellular extensions and neurosecretory granules containing peptides and neuropeptides, lack androgen receptors, release mitogenic factors and are highly aggressive. Increase in cAMP, induces NE trans-differentiation (FIG. 1).

Figure 2:
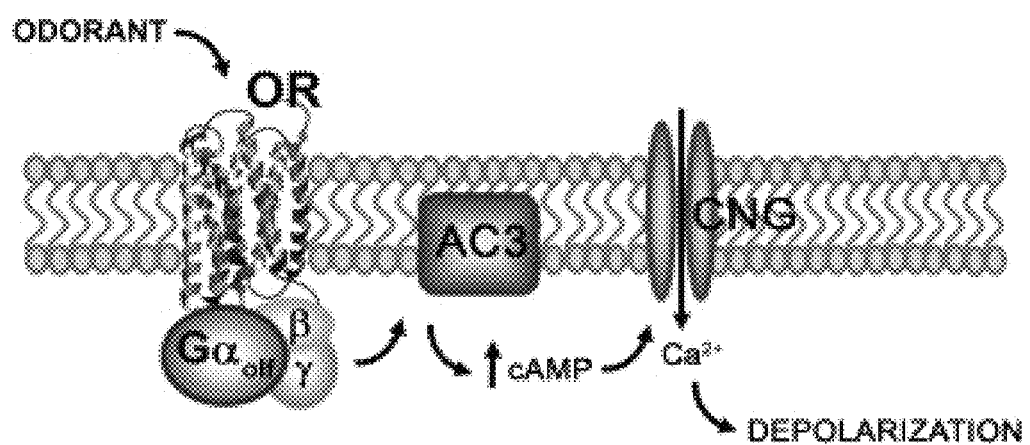
FIG. 2 is a schematic showing the odorant receptor (OR) and neighboring transmembrane proteins involved in the signaling in the olfactory neurons.

Prostate-Specific G-Protein Coupled Receptor (PSGR/OR51E2): Odorant receptors, also known as olfactory receptors, are G-protein coupled receptors (GPCRs) found in the brain, skeletal muscle, gastrointestinal tract, sperm, and other tissues. Olfactory receptors share a seven-transmembrane domain receptors, and are responsible for the recognition and G protein-mediated transduction of odorant signals. Olfactory signaling generates increase in cellular cAMP, which creates action potentials in the olfactory neurons. OR51E2 expression in prostate tissue increases as prostate cancer progresses. As disclosed herein, activation of OR51E2 increases expression of neuroendocrine markers, and thus NE-like cells (FIG. 2).

As disclosed herein, OR51E2/PSGR is a therapeutic target for treating, preventing, and diagnosing castrate-resistant prostate cancer (CRPC). In silico (homology modeling and virtual ligand screening) and in vitro (heterologous cell expression system and luciferase assay) approaches were used to identify and validate modulators (agonists, antagonists, partial antagonists, and inverse agonists) of OR51E2/PSGR.

As used herein, the term "prostate cancer" refers to cancer that occurs in the prostate gland and includes, but is not limited to, benign prostatic hyperplasia (BPH), prostatic adenocarcinoma, small cell carcinoma, squamous cell carcinoma, prostatic sarcomas, transitional cell carcinomas, and castrate-resistant prostate cancer (CRPC) (also referred to as androgen independent prostate cancer). Human prostate cancer cell lines used to research prostate cancer include, but are not limited to, DU145 cells, LNCaP cells and PC-3 cells.

As used herein, the terms "modulator" and "ligand" are used interchangeably to refer to an agent that is capable of positively or negatively impacting basic cellular functions, such as cell proliferation, progression, growth, spread, survival, and/or motility, and is involved in metabolic homeostasis, inflammation, or angiogenic processes. Furthermore, a modulator or a ligand is a substance that forms a complex with a biomolecule to serve a biological purpose. In protein-ligand binding, for example, the ligand is usually a molecule that induces a signal upon binding to a site on a target protein. The binding typically results in a change of conformation of the target protein. Modulator or ligand binding to a receptor protein, such as OR51E2, alters the chemical conformation by affecting the three-dimensional shape orientation. The conformation of a receptor protein composes the functional state. Modulator or ligand binding to a receptor protein, such as OR51E2, can also alter expression patterns or levels of the receptor.

Modulators and ligands include substrates, inhibitors, activators, neurotransmitters, agonists, antagonists, inverse agonists, inverse antagonists, partial agonists, and partial antagonists. Modulators and ligands include, but are not limited to, chemical compounds, such as endogenous metabolites, non-endogenous metabolites, and synthetic chemical compounds, polypeptides, amino acid residues, nucleic acids, siRNA, and antibodies. Examples of modulators and ligands of OR51E2 include, but are not limited to, estriol, epitestosterone, 19-OH AD (19-hydroxyandrost-4-ene-3,17-dione), palmitic acid, androstenedione, D-alanyl-d-alanine, glycylglycine, kojibiose, urea, AFMK (N-acetyl-N-formyl-5-metoxykynurenamine), pelargonidin, hydroxypyruvic acid, adenosine 2',3'-cyclic phosphate, gamma-CEHC, tetrahydrocurcumin, N-acetylglutamic acid, L-histidinol, bradykinin, 8-Hydroxyguanine, imidazolone, 2-pyrrolidinone, 2-ketoglutaric acid, L-glyceric acid, glycine, propionic acid, and 13-cis retinoic acid, and isomers thereof.

In certain embodiments, the OR51E2 ligand is 13-cis retinoic acid, and isomers thereof.

Included within the scope of the modulators and ligands of the disclosure are derivatives of modulators and ligands, such as isotope variants, substitution variants, and the like, as well as derivatives designed to provide for more favorable properties in vitro or in vivo. In a non-limiting example, the modulators and ligands may be covalently bound to a biologically acceptable polymer.

As used herein, the term "agonist" refers to a modulator or ligand that binds to a receptor and activates the receptor to produce a biological response. OR51E2 agonists can be identified by the in silico and in vitro assays described herein. Examples of OR51E2/PSGR agonists include, but are not limited to, estriol, epitestosterone, 19-OH AD (19-hydroxyandrost-4-ene-3,17-dione), palmitic acid, androstenedione, D-Alanyl-d-alanine, glycylglycine, kojibiose, urea, AFMK (N-acetyl-N-formyl-5-metoxykynurenamine), pelargonidin, hydroxypyruvic acid, adenosine 2',3'-cyclic phosphate, gamma-CEHC, tetrahydrocurcumin, N-acetylglutamic acid, L-histidinol, bradykinin, 8-Hydroxyguanine, imidazolone, 2-pyrrolidinone, 2-ketoglutaric acid, L-glyceric acid, glycine, and propionic acid, and isomers thereof.

As used herein, the term "antagonist" refers to a modulator or ligand that blocks, impedes, or dampens a biological response by binding to and blocking a receptor rather than activating it. OR51E2 antagonists can be identified by the in silico and in vitro assays described herein. Examples of OR51E2/PSGR antagonists include, but are not limited to 13-cis retinoic acid (13-cis RA), and isomers thereof.

As used herein, the term "inverse agonist" refers to a modulator or ligand that binds to the same receptor as an agonist but induces a biological response opposite to that agonist. OR51E2 inverse agonists can be identified by the in silico and in vitro assays described herein. Examples of OR51E2/PSGR inverse agonists include, but are not limited to, 13-cis retinoic acid (13-cis RA), and isomers thereof.

As use herein, the term "partial antagonist" refers to a modulator or ligand that can bind to a receptor but does not completely block the receptor's effects, but rather decreases the maximum potential of the receptor. OR51E2 partial antagonists can be identified by the in silico and in vitro assays described herein. Examples of OR51E2/PSGR partial antagonists include, but are not limited to, and 13-cis retinoic acid (13-cis RA), and isomers thereof.

Identification of PSGR/OR51E2 modulators and their effect on prostate cancer cell phenotype can be investigated using cell viability/proliferation assays and by analyzing metabolomics signatures of neuroendocrine differentiation.

Chronic agonist-mediated activation of the OR51E2/PSGR receptor can turn this receptor into an oncogene/oncoprotein, and thereby facilitate cellular transformation resulting in neuroendocrine trans-differentiation (NEtD), a characteristic phenotype of castrate resistant prostate cancer (CRCP). An oncogene is a gene that has the potential to cause cancer, and in tumor cells, oncogenes can be mutated and/or expressed at high levels. Inhibitors or antagonists and inverse agonists of the OR51E2/PSGR receptor may be used as novel therapeutic agents, in order to slow down NEtD progression in the late stage of CRCP.

One aspect of the present disclosure provides a method of treating prostate cancer or preventing the progression of prostate cancer in a subject in need thereof, comprising: administering to a subject a therapeutically effective amount of one or more OR51E2 ligands, wherein the ligand binds to OR51E2 on a prostate cancer cell and impedes the progression of the prostate cancer cell.

As used herein, the terms "treating" and "treatment" are used interchangeably to refer to both therapeutic treatment and prophylactic or preventative measures. It refers to curing, attenuating, alleviating, minimizing, or suppressing the deleterious effects of a disease state, disease progression, disease causative agent (e.g., bacteria or viruses), or other abnormal condition.

As used herein, the terms "preventing" and "prevention" are used interchangeably to refer to impeding, delaying, halting, or reversing the progression of a disease, such as prostate cancer. For example, preventing prostate cancer can mean preventing a prostate cancer cell from differentiation into NE-like cells, a characteristic phenotype of CRCP.

The term "progression" or "tumor progression" as used herein refer to the growth, development, differentiation, and proliferation of prostate tumor cells at any stage and grade. In some embodiments, progression refers to the advancement from normal prostate epithelial cells to pre-invasive lesions. In some embodiments, progression refers to the advancement of indolent tumors to aggressive tumors. In some embodiments, tumor progression can be characterized by increased growth speed and invasiveness of the prostate tumor cells. As a result of progression, phenotypical changes occur and the prostate tumor can become more aggressive and acquires greater malignant potential. In other embodiments, progression refers to the differentiation of prostate epithelial cells into neuroendocrine-like cells (NEtD), a characteristic phenotype of CRCP.

As used herein, the term "therapeutically effective amount" generally refers to an amount of an OR51E2 ligand sufficient to affect a desired biological response. Such response may be a beneficial result, including, without limitation, amelioration, reduction, prevention, or elimination of symptoms of a disease or disorder. Therefore, the total amount of each active component of the OR51E2 ligand is sufficient to demonstrate a meaningful benefit in the patient, including, but not limited to, treatment of prostate cancer. A "therapeutically effective amount" may be administered through one or more preventative or therapeutic administrations. When the term "therapeutically effective amount" is used in reference to a single agent, administered alone, the term refers to that agent alone, or a composition comprising that agent and one or more pharmaceutically acceptable carriers, excipients, adjuvants, or diluents. When applied to a combination, the term refers to combined amounts of the active agents that produce the therapeutic effect, or composition(s) comprising the agents, whether administered in combination, consecutively, or simultaneously. The exact amount required will vary from subject to subject, depending, for example, on the species, age, and general condition of the subject; the severity of the condition being treated; and the mode of administration, among other factors known and understood by one of ordinary skill in the art. An appropriate "effective" amount in any individual case may be determined by one of ordinary skill in the art. Thus, a "therapeutically effective amount" will typically fall in a relatively broad range that can be determined through routine trials.

The OR51E2 ligands described herein may be administered by any suitable route of administration. In certain embodiments, an OR51E2 ligand is administered intravenously, subcutaneously, transdermally, intradermally, intramuscularly, orally, transcutaneously, or intraperitoneally (IP). The OR51E2 ligands may be administered as a composition comprising the ligand and one or more pharmaceutically acceptable carriers, excipients, adjuvants, or diluents.

As used herein, the terms "patient," "individual," or "subject" are used interchangeably and are intended to include human and non-human animals. Exemplary human subjects include a human patient suffering from prostate cancer, and CRCP in particular. Exemplary human patients may also be suffering from chronic or acute infections or inflammation, such as chronic post-operative prosthetic joint infections, osteomyelitis, endocarditis, and chronic prostatitis, caused by an infection by a bacterium, such as P. acnes. The term "non-human animals" includes all vertebrates, e.g., non-mammals (such as chickens, amphibians, reptiles) and mammals, such as non-human primates, domesticated and/or agriculturally useful animals (such as sheep, dogs, cats, rabbits, cows, pigs, etc.), and rodents (such as mice, rats, hamsters, guinea pigs, etc.).

In some embodiments, the subject suffers from chronic infection or chronic inflammation.

Chronic infection occurs when the immune system is unable to respond to the infective agent or pathogen. Chronic infection can be caused by viral, bacterial, or fungal infections. Chronic infections can occur for a variety of reasons, for example, the pathogen might find a way to hide itself within the body. Examples of chronic infections include, but are not limited to, chronic fatigue syndrome, Epstein barr virus, mycoplasma, HIV, hepatitis, herpes, chronic post-operative joint infections, such as osteomyelitis and endocarditis, prostatitis, bladder infections, chlamydia, and urinary tract infections. In certain embodiments, the subject suffers from a chronic infection caused by P. acnes.

Chronic inflammation can be long-term inflammation and can last for several months or years. Chronic inflammation can result from a failure to eliminate the cause of an acute inflammation, an autoimmune response to a self-antigen, or exposure to a low level of a particular irritant, such as a chemical, over a long period of time. Examples of chronic inflammation include, but are not limited to, asthma, chronic peptic ulcer, tuberculosis, rheumatoid arthritis, chronic periodontitis, ulcerative colitis, Crohn's disease, chronic sinusitis, and chronic active hepatitis.

Another aspect of the present disclosure provides a method of impeding the progression of a prostate cancer cell, comprising contacting the prostate cancer cell with one or more OR51E2 ligands.

Yet another aspect of the present disclosure provides a method of diagnosing prostate cancer in a subject, comprising: a) obtaining a biological sample from the subject; b) contacting the sample with one or more OR51E2 ligands; c) detecting an increase and/or decrease in the level of one or more metabolites associated with ligand-bound OR51E2 in the sample as compared to a sample not contacted with one or more OR51E2 ligands; and d) identifying the presence of prostate cancer based on the increase or decrease of said metabolites.

The biological sample may be any component extracted from the subject, including, but not limited to, blood, serum, plasma, urine, and tissue.

Metabolites associated with ligand-bound OR51E2 include, but are not limited to, 2-deoxyglucose, 2-ketoleucine, 3-phosphoglyceric, adenosine/inosine, alanine, alpha ketoglutaric, asparagine, aspartic acid, benzoic acid, beta-alanine, cystine, dehydroalanine, ethanolamine, fructose-6-phosphate, fumaric acid, glucose-6-phosphate, glutamic acid, glutamine, glutaric acid, glyceric acid, glycine, guanine, hydroquinone, hydroxyprolines, inosine, lactic acid, lactose, lysine, malic acid, N-acetylaspartic, oleic acid, O-methylphosphate, ornithine, pantothenic acid, pentonic acids, phenylalanine, phosphoenolpyruvate, serine, spermidine, spermine, succinic acid, threitol/erythritol, threonine, threose/erythrose, tyramine, tyrosine, urea, uric acid, and xanthine.

Metabolomics signatures or metabolite profiles of prostate cancer cells include, but are not limited to, lactic acid, serine, threonine, glucose-6 phosphate, fructose-6 phosphate, fumaric acid, glutamic acid, beta-alanine, ornithine, or inosine. In some embodiments, the presence of NEtD of prostate cancer cells can be indicated by a decrease in the intracellular level of the above-mentioned metabolites, and an increase in intracellular phosphoenolpyruvate, and increase in extracellular levels of cystine, aparagine, glutaric acid, guanine, glutamine following treatment with an agonist as compared to prostate cancer cells that were untreated.

As used herein, the term "diagnose" refers to identifying the nature of a medical condition of a subject, such as prostate cancer, including castrate resistant prostate cancer, from its signs and symptoms.

The following examples are offered by way of illustration and not by way of limitation.

Figure 3:
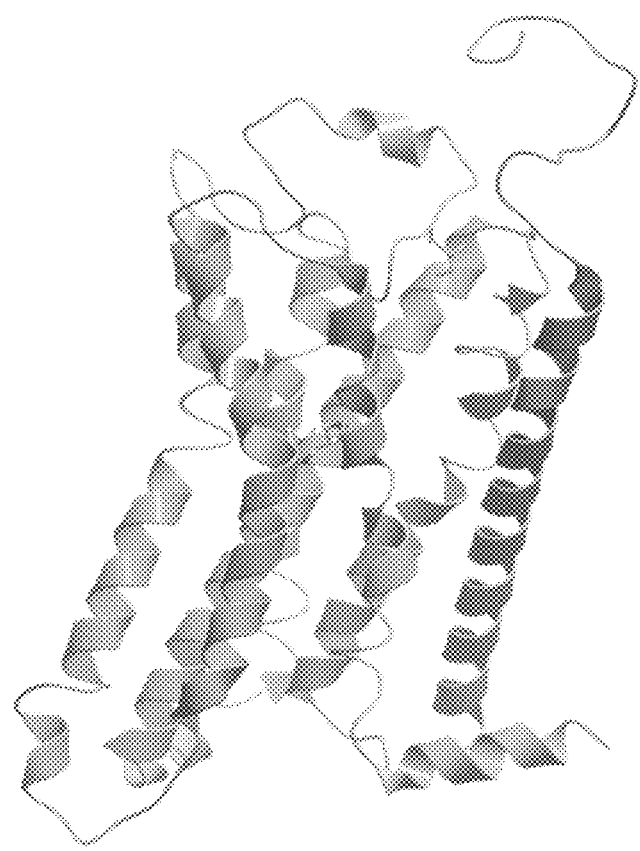
FIG. 3 is a homology model of OR51E2.

Example 1: Identification of Biologically Relevant OR51E2/PSGR Metabolite-Ligands in Silico To discover new, biologically relevant ligands for OR51E2/PSGR, a homology modeling and an in silico ligand screening approach of a metabolite library was applied. The Modeller v.9.14 program was used to produce a model of OR51E2 based on the crystal structure of the β2 adrenergic receptor. Twenty models were made using an automodel script and each model was assessed with DOPE score. The best model was used for virtual ligand screening (VLS) with ICM Software (MolSoft v.3.8, LLC). Homology model of OR51E2 is shown in FIG. 3.

Figure 4:
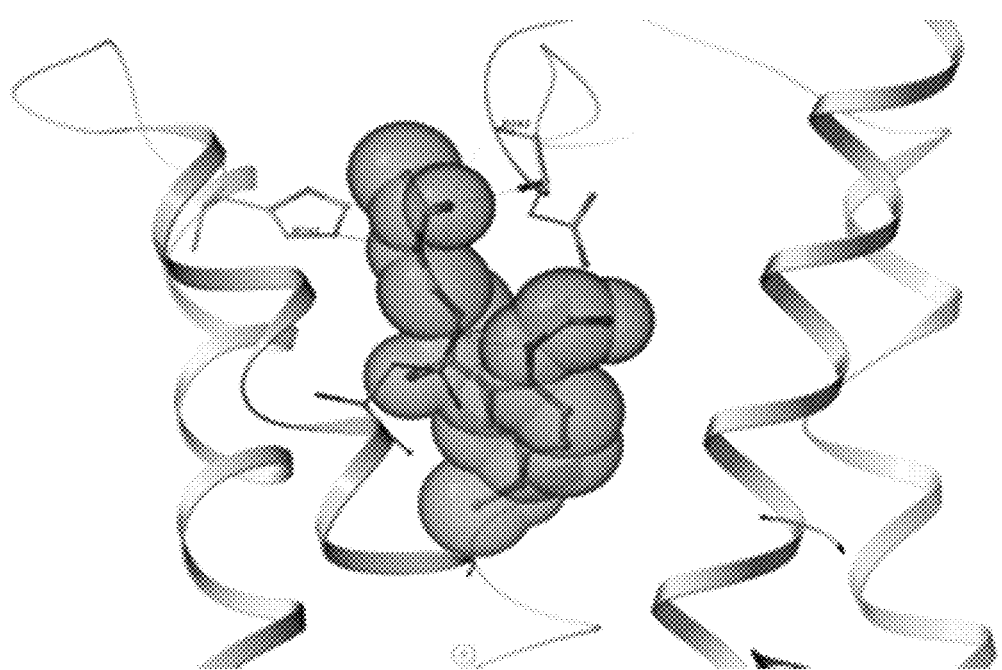
FIG. 4 is a homology model showing the preferred docking conformation of the AFMK ligand.

A library of 2,511 human metabolites were selected from the Human Metabolome Database (www.HMDB.ca) and virtually screened against a homology model of OR51E2/PSGR. The VLS result lists metabolites according to their scores, which represent the predicted binding of the ligand to the receptor. Results from the VLS, for example, showed the preferred docking conformation of acetyl-2-formyl-5-methoxykynurenamine (AFMK) ligand bound to OR51E2 (FIG. 4).

The identification of agonists and antagonists, selected from a library of human metabolites as opposed to virtually designed compounds, will unravel specific pathways that can be modulated to reverse NEtD of cancer cells.

Example 2: Effect of Biologically Relevant OR51E2/PSGR Metabolite-Ligands on Metabolism in Prostate Cancer Cells In Vitro To determine whether OR51E2/PSGR activation mediates neuroendocrine trans-differentiation (NEtD), which is characteristic for castrate resistant prostate cancer, CRPC, an in vitro luciferase assay was used to validate the top ligand candidates identified by the in silico method described in Example 1.

Luciferase Assay

Figure 5:
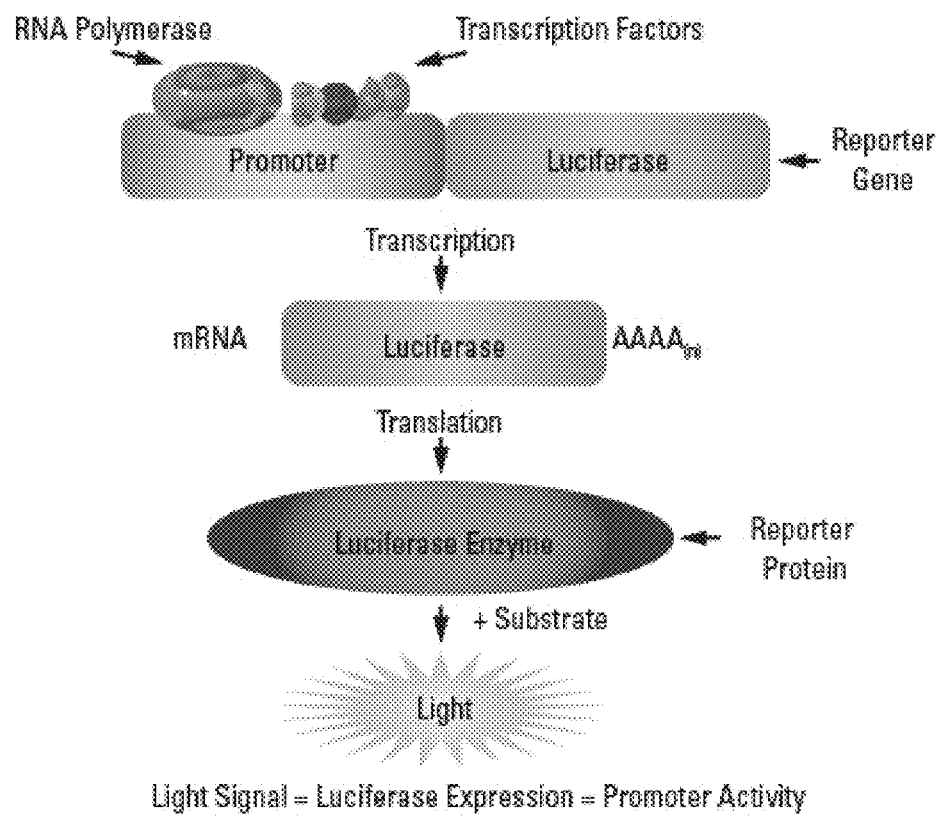
FIG. 5 is a general schematic of a luciferase assay. (ThermoFisher Scientific, Luciferase Reporters, Protein Biology Resource Library, available at www.thermofisher.com/sa/en/home/life-science/protein-biology/protein-biology-learning-center/protein-biology-resource-library/pierce-protein-methods/luciferase-reporters.html).
Figure 6:
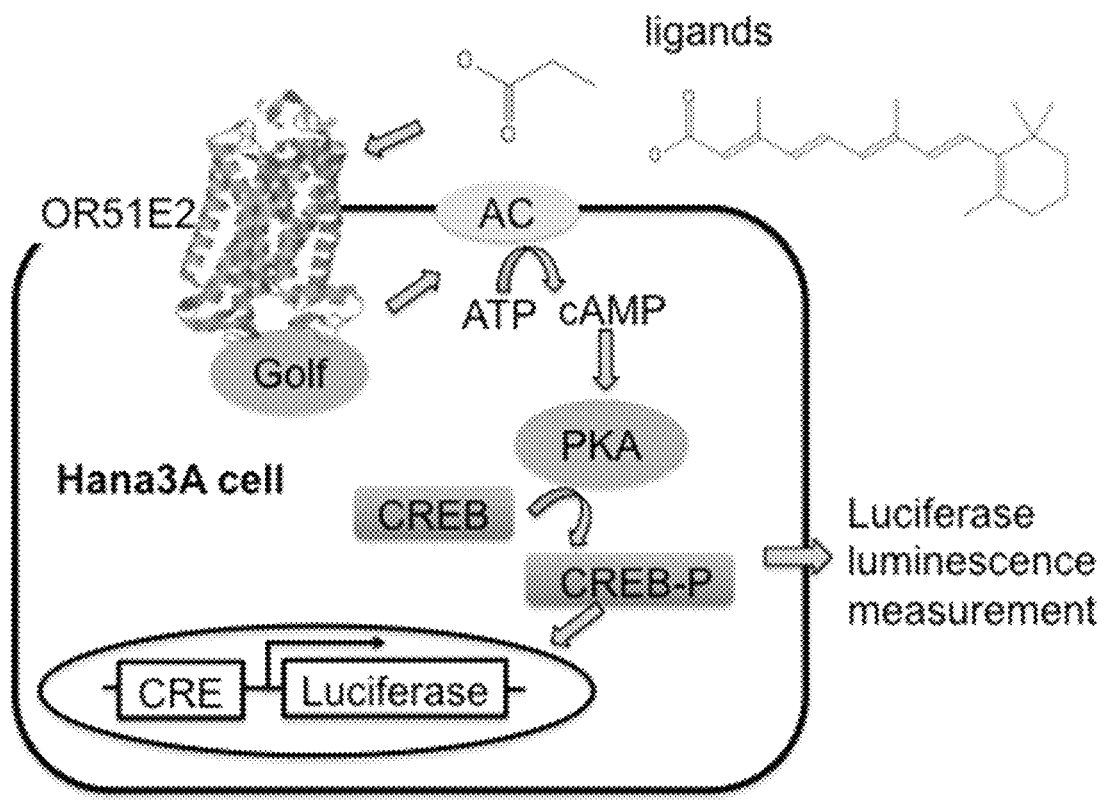
FIG. 6 is a schematic of the in vitro luciferase assay used to test the potency of OR51E2 ligands (adapted from Zhuang et al. (2008) *Nature Protocols* 3:1402-13).

Hana3A cells (modified human embryonic kidney cells) were cultured in 96 well plates in M10PSF medium. LNCaP human prostate cancer cells were cultured in both RPMI medium and androgen deprived RPMI medium. Hana3A cells were transfected with CRE-Luc (CREB-dependent luciferase (Firefly)) and SV40-RL promoter plasmids, and pCI and OR51E2 plasmids. Hana3A cells were then stimulated with ligands that were identified in the virtual screen process of Example 1. Upon ligand binding, an increase in cAMP drives the expression of Firefly luciferase. Increase in luminescence signal was measured with a luminometer and Optima Data Analysis software. The luminescent signal is directly proportional to receptor activation. A general schematic of a luciferase assay is shown in FIG. 5 and a schematic of the assay used in this Example is shown in FIG. 6.

Figure 7:
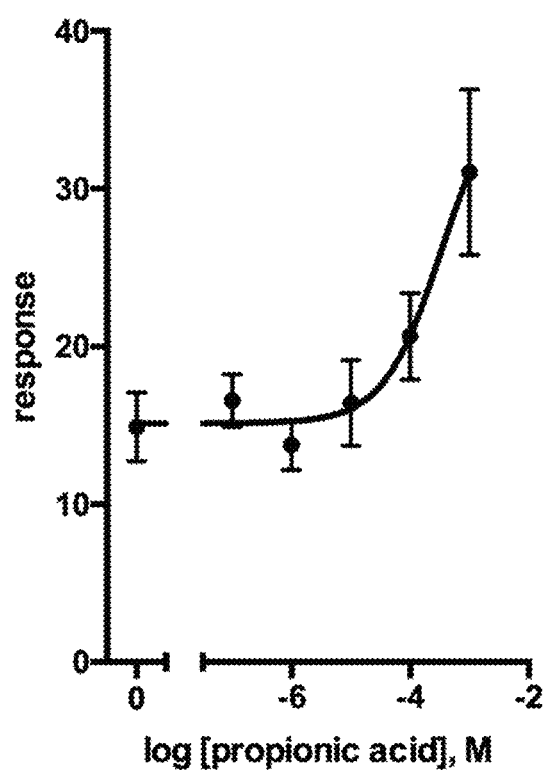
FIG. 7 is a dose-response curve showing the effect of propionic acid on OR51E2 receptor activation.

The top 56 compounds from the VLS list were tested using the in vitro expression and luciferase assay. The potency of the most promising agonist and antagonist was determined by calculating their $EC_{50}$ and $IC_{50}$, respectively. The biologically relevant concentrations of each metabolite were individually determined based on available data in the literature. If no data were available, compounds were tested in the range of 1 nM-100 μM. Responses were normalized to the response with 1 mM propionic acid (PA), a previously identified agonist, and also to a response with no-control. The effect of PA on OR51E2 is shown in the dose-response curve of FIG. 7.

Results

Figure 8:
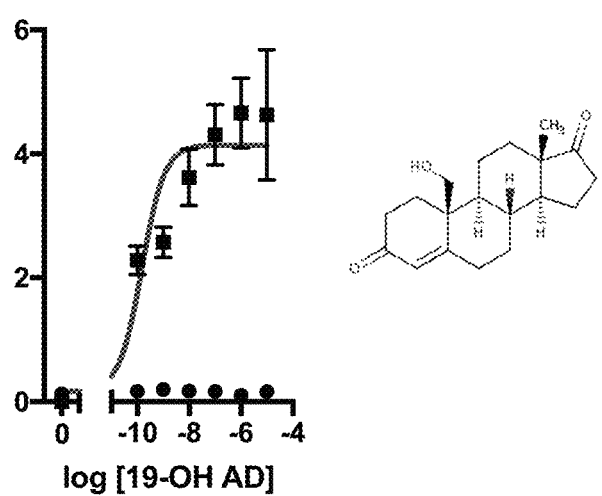
FIG. 8 is a dose-response curve showing the effect of 19-OH AD on OR51E2 receptor activation. Responses are normalized to the responses with no-agonist control. Results are mean+/−SEM, n=6.
Figure 9:
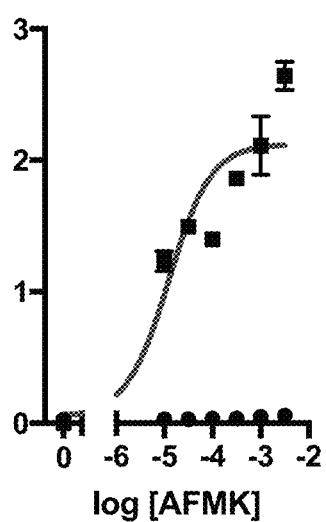
FIG. 9 is a dose-response curve showing the effect of AFMK on OR51E2 receptor activation.
Figure 9:
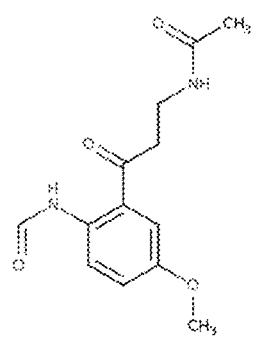
Figure 10:
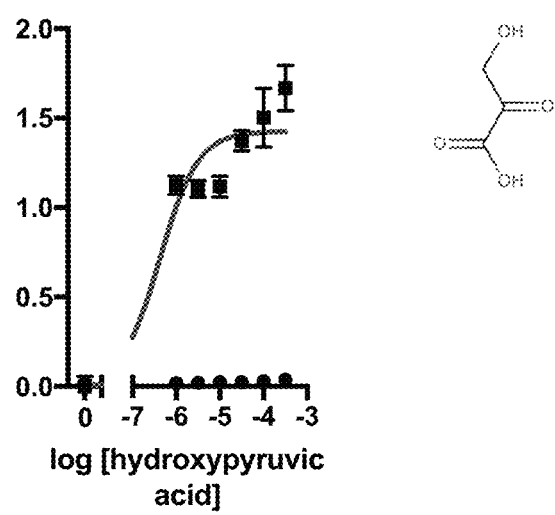
FIG. 10 is a dose-response curve showing the effect of hydroxy pyruvic acid on OR51E2 receptor activation.
Figure 11:
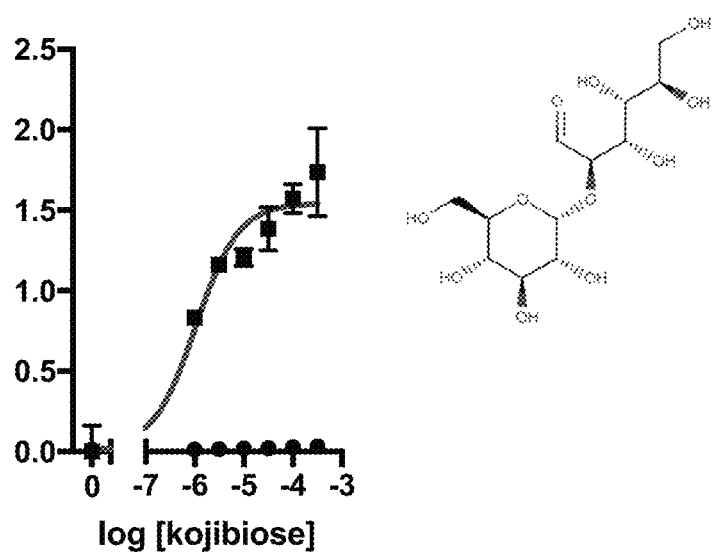
FIG. 11 is a dose-response curve showing the effect of kojibiose on OR51E2 receptor activation.
Figure 12:
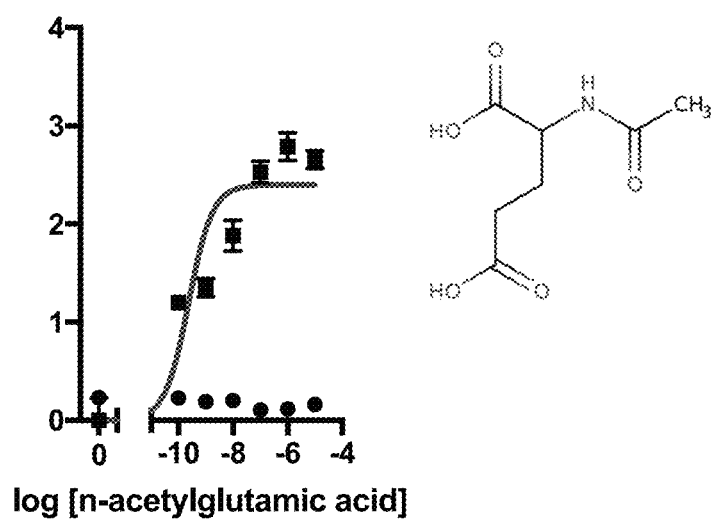
FIG. 12 is a dose-response curve showing the effect of n-acetylglutamic acid on OR51E2 receptor activation.
Figure 13:
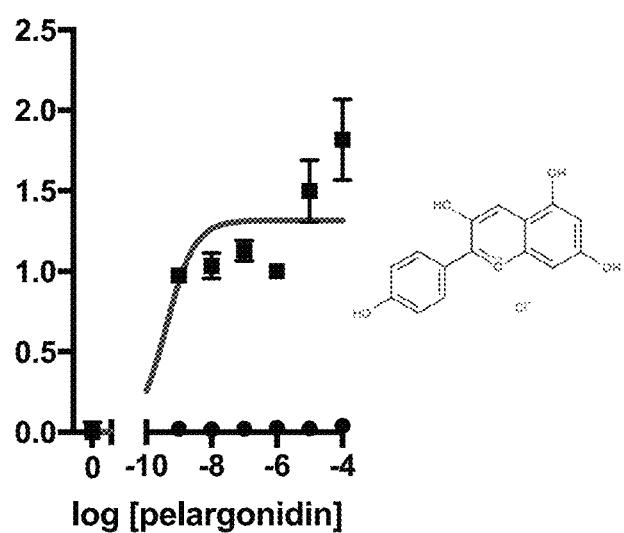
FIG. 13 is a dose-response curve showing the effect of pelargonidin on OR51E2 receptor activation.
Figure 14:
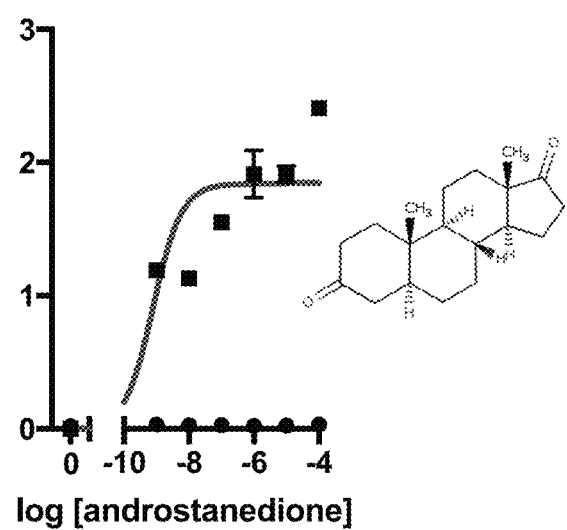
FIG. 14 is a dose-response curve showing the effect of androstanedione on OR51E2 receptor activation.
Figure 15:
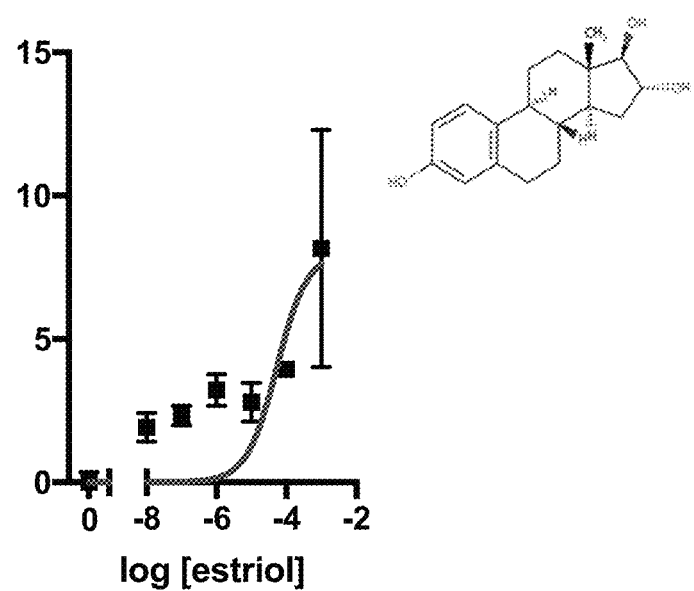
FIG. 15 is a dose-response curve showing the effect of estriol on OR51E2 receptor activation.
Figure 16:
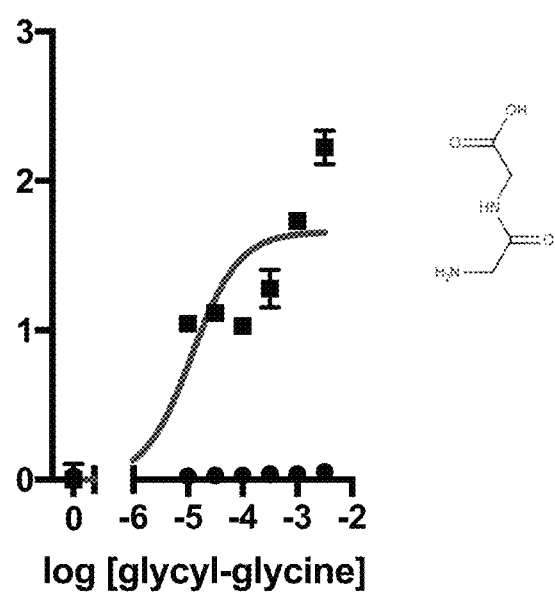
FIG. 16 is a dose-response curve showing the effect of glycyl-glycine on OR51E2 receptor activation.

Twenty four (24), new potent OR51E2 agonists and one potent OR51E2 antagonist were identified. The dose response curves for several OR51E2 agonists are presented here in the figures indicated after each compound: 19-OHAD (19-hydroxyandrostenedione) (FIG. 8), AFMK (acetyl-2-formyl-5-methoxykynurenamine) (FIG. 9), hydroxypyruvic acid (FIG. 10), kojibiose (FIG. 11), N-acetylglutamic acid (FIG. 12), pelargonidin (FIG. 13), androstanedione (FIG. 14), estriol (FIG. 15), and glycylglycine (FIG. 16). The $EC_{50}$ values and efficacy (when compared to the 1 mM PA response) for all identified OR51E2 agonists are provided in Table 1.

TABLE 1

Potency ($EC_{50}$) and efficacy of OR51E2 Agonists

| Agonist Name | HMDB | CAS | $EC_{50}$ (potency) [M] | Max conc. used | Efficacy |
|---|---|---|---|---|---|
| Estriol | HMDB00153 | 50-27-1 | 5.30E−05 | 10 μM | 0.344 |
| Epitestosterone | HMDB00628 | 481-30-1 | 6.90E−10 | 10 μM | 0.477 |
| 19-OH AD (19-hydroxyandrost-4-ene-3,17-dione) | HMDB03955 | 510-64-5 | 1.50E−10 | 10 μM | 0.890 |
| Palmitic acid | HMDB00220 | 57-10-3 | 9.80E−09 | 1 mM | 0.927 |
| Androstanedione | HMDB00899 | 846-46-8 | 7.90E−10 | 100 μM | 0.888 |
| D-Alanyl-d-alanine | HMDB03459 | 923-16-0 | 1.40E−05 | 3.16 mM | 1.505 |
| Glycylglycine | HMDB11733 | 556-50-3 | 1.10E−05 | 3.16 mM | 1.797 |
| Kojibiose | HMDB11742 | NA | 1.00E−06 | 316 μM | 0.790 |
| Urea | HMDB00294 | 57-13-6 | 2.30E−08 | 10 mM | 0.580 |
| AFMK (N-acetyl-N-formyl-5-metoxykynurenamine) | HMDB04259 | 52450-38-1 | 1.20E−05 | 3.16 mM | 1.483 |
| Pelargonidin | HMDB03263 | 134-04-3 | 4.20E−10 | 100 μM | 0.621 |
| Hydroxypyruvic acid | HMDB01352 | 1113-60-6 | 4.20E−07 | 316 μM | 1.100 |
| Adenosine 2',3'-cyclic phosphate | HMDB11616 | 634-01-5 | 2.60E−08 | 3.16 μM | 1.025 |
| Gamma-CEHC | HMDB01931 | 178167-77-6 | 6.40E−09 | 10 μM | 1.286 |
| Tetrahydrocurcumin | HMDB05789 | 36062-04-1 | 5.70E−07 | 316 μM | 0.284 |
| N-Acetylglutamic acid | HMDB01138 | 1188-37-0 | 2.30E−10 | 10 μM | 0.879 |
| L-Histidinol | HMDB03431 | 4836-52-6 | 3.50E−11 | 100 μM | 0.578 |
| Bradykinin | HMDB04246 | 58-82-2 | 1.30E−09 | 100 μM | 0.762 |
| 8-Hydroxyguanine | HMDB02032 | 5614-64-2 | 4.40E−13 | 100 nM | 0.570 |
| Imidazolone* | HMDB04363 | 1192-34-3 | 7.60E−12 | 10 μM | 0.678 |
| 2-Pyrrolidinone | HMDB02039 | 616-45-5 | 1.90E−09 | 100 μM | 0.525 |
| 2-Ketoglutaric acid | HMDB00208 | 328-50-7 | 5.50E−09 | 1 mM | 0.594 |

TABLE 1-continued

Potency (EC$_{50}$) and efficacy of OR51E2 Agonists

| Agonist Name | HMDB | CAS | EC$_{50}$ (potency) [M] | Max conc. used | Efficacy |
|---|---|---|---|---|---|
| L-Glyceric acid | HMDB06372 | 28305-26-2 | 1.90E−09 | 1 mM | 0.898 |
| Glycine | HMDB00123 | 56-40-6 | 5.80E−08 | 1 mM | 0.613 |

Figure 17:
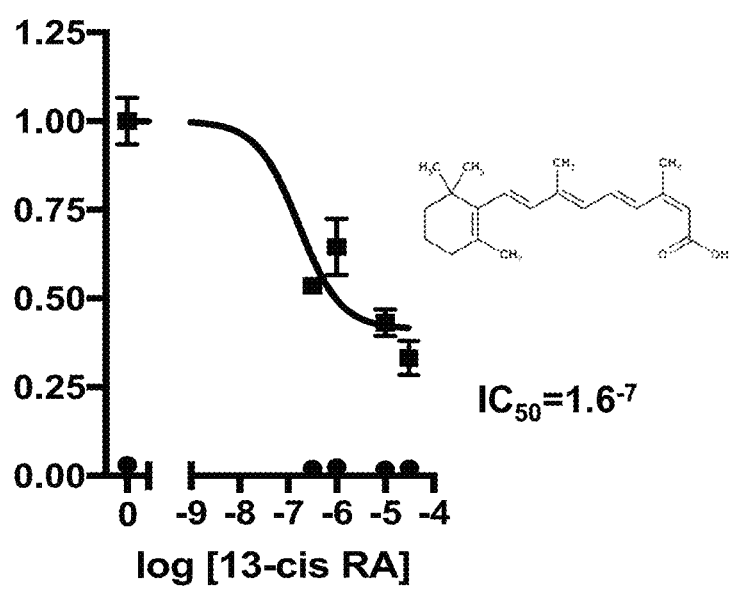
FIG. 17 is a dose-response curve showing the antagonistic effect of 13-cis RA on OR51E2 receptor activation. Responses have been normalized to the responses with 1 mM PA. Results are mean+/−SEM, n=3.

Additionally, 13-cis retinoic acid (13-cis RA) was identified as a potent OR51E2 antagonist with an IC$_{50}$ value of 160 nM. A dose response curve for 13-cis RA is shown in FIG. 17.

Figure 18:
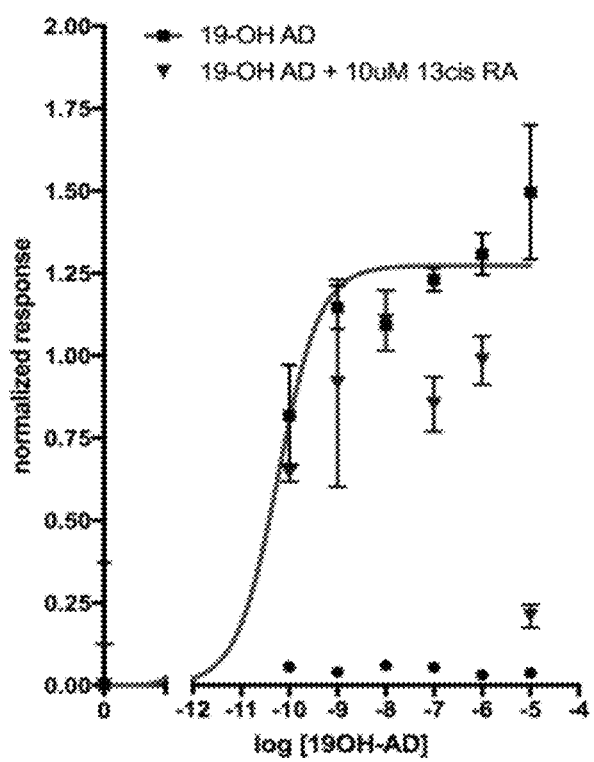
FIG. 18 is a dose-response curve showing the effect of 19-OHAD on OR51E2 receptor activation in the absence (square) and presence (triangle) of 13 cis-RA.

19-OH AD was also tested in Hana3A cells expressing OR51E2 in the absence and presence of the 13-cis retinoic acid antagonist, further demonstrating the potency of 13-cis RA as an inhibitor of OR51E2. (FIG. 18).

Discussion

Figure 19:
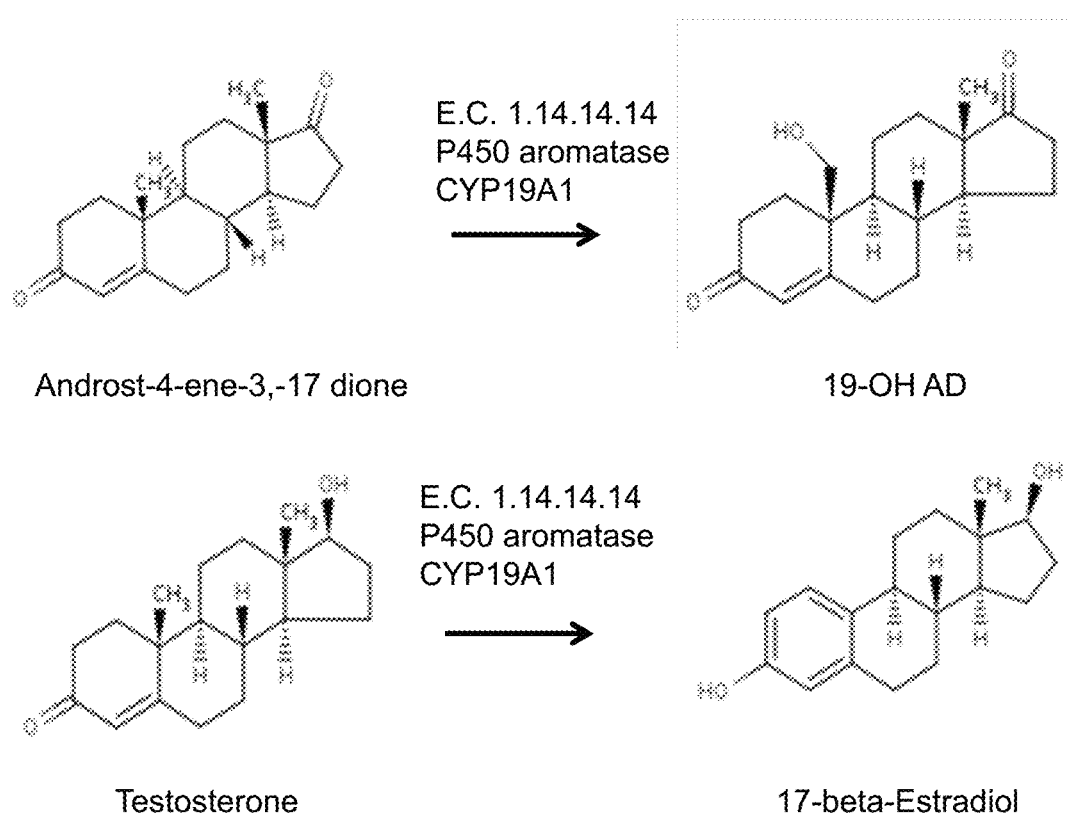
FIG. 19 is a schematic showing the production of 19-OH AD by P450 aromatase.

19-OH AD was one of the most potent agonist identified from the ligand screen, as indicated by an EC$_{50}$ of 1.5e$^{-10}$ M (FIG. 8 and Table 1). 19-OH AD is produced by the enzyme P450 aromatase (CYP19A1), a highly up-regulated enzyme in prostate cancer (PCa) (FIG. 19), indicating that 19-OH AD is a biologically relevant agonist. Furthermore, 19-OH AD amplifies the effects of the renin-angiotensin system (RAS), a system that, when over activated, causes hypertension. All RAS components have been identified in the prostate and angiotensin II was shown to have a role in prostate cancer development. The correlation between 19-OH AD, RAS and prostate cancer indicates a relationship between 19-OH AD, activation of OR51E2 and prostate cancer.

The other agonists identified by this assay are also biologically relevant. AFMK, a metabolite of kynurenamine, was previously reported to be abundantly present in aggressive prostate cancers. AFMK mitigates damage to DNA through anti-oxidative effects. AFMK's role in mitigating the adverse effects of cancer indicates its involvement in prostate cancer.

Glycyl-glycine has been detected in the plasma of patients with prostate cancer. Glycyl-glycine metabolism occurs in digestion and produces glycine. A derivative of glycine is sarcosine, a biomarker for prostate cancer. Further research could support the role of glycyl-glycine activation of OR51E2 in prostate cancer development.

Kojibiose has been detected in the plasma of patients with prostate cancer. Its prevalence in prostate cancer may point to a potential relationship between kojibiose activation of OR51E2 and prostate cancer development.

Furthermore, the results indicate that 13-cis RA can act via the OR51E2 receptor. Isotretinoin, or 13-cis RA, is a potent oral retinoid used for the treatment of severe acne, and is effective against *P. acnes* bacterium. 13-cis RA could be an inhibitor of OR51E2 to treat prostate cancer. Previously, Dahiya et al. investigated effects of 13-cis RA on LNCaP cells and found it inhibits cell growth and decreases tumorigenic potential. (Dahiya et al. (1994) *Int. J. Cancer* 59(1):126-132).

In addition, propionic acid effects on prostate cancer cells will be studied, as it was previously identified as agonist for PSGR/OR51E2. Alpha-ionone, an antagonist, will also be tested.

The biologically relevant OR51E2 ligands identified by this in vitro assay can be used as therapeutic and diagnostic agents for prostate cancer. Additionally, this assay is a useful in vitro model to study neuroendocrine trans-differentiation of prostate cancer cells.

Figure 20:
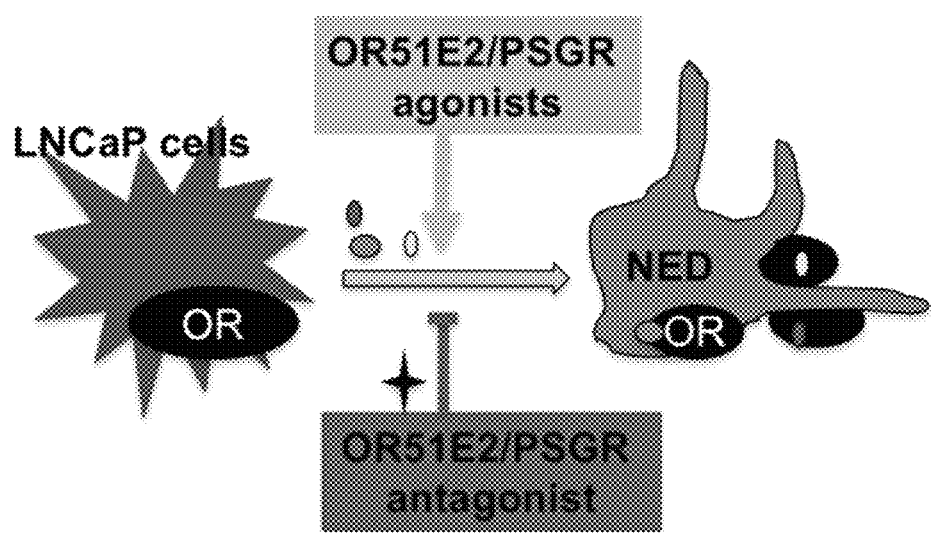
FIG. 20 is a schematic of the in vitro assays used to study neuroendocrine trans-differentiation in prostate cancer cells via the activation of OR51E2/PSGR with endogenous metabolites.

Example 3: Effect of Biologically Relevant OR51E2/PSGR Metabolite-Ligands on Expression Signatures in Prostate Cancer Cells In Vitro To further determine whether OR51E2/PSGR activation mediates neuroendocrine trans-differentiation (NEtD), prostate cancer cells were treated with selected metabolite-ligands and their metabolomics signatures, expression of NE-markers, and viability and proliferation were analyzed. (FIG. 20).

In Vitro Expression and Metabolomics Signature Assays

To assess the differentiation status of LNCaP cells following treatment with an OR51E2 ligand, cells were exposed to the ligands for three days. Biological markers of NED were analyzed using an RT-PCR assay. The following markers were tested: neuron specific enolase (NSE) and α-methylacyl-CoA racemase (AMACR), an enzyme essential for isomerization of branched-chained fatty acids that is present at low levels in healthy prostate cells and increased in PCa and in NE-like cells. Furthermore, changes in the expression levels of OR51E2 and androgen receptor (AR) were determined. This experiment will also be conducted using RWPE-2 cells.

Expression of keratins K5, K8, and K18 will also be assessed, as RWPE-2 cells are positive for K8 and K18. LNCaP cells are positive for K18, and NE cells express K5.

Metabolomics signatures were assessed using untargeted gas chromatography/mass spectrometry (GC/MS) to analyze LNCaP cells treated with an OR51E2 ligand for 3 days. There were six biological replicates for each treatment and the results were analyzed using MetaboAnalyst software. The same analysis will also be conducted using RWPE-2 cells.

The NEtD status was assessed through analysis of viability and proliferation of LNCap cells using use CellTiter-Glo Luminescent cell viability assay (Promega). Reduced proliferation with agonist treatment will occur because NE-like cells do not proliferate. Viability and proliferation assays will also be conducted with OR51E2 ligands in RWPE-2 cells.

The OR51E2 gene will be knocked down using an siRNA interference approach in order to confirm that the observed effects are indeed receptor-specific.

Results

Figure 21A:
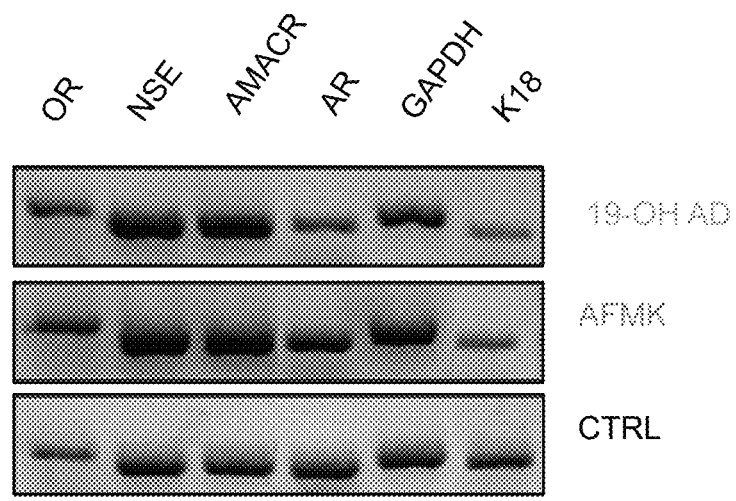
FIG. 21A is a representative gel image showing transcript levels of several genes after 12 days incubation with 19-OH AD and AFMK, as compared to control by RT-PCR analysis. OR: OR51E2, NSE: neuron specific enolase, AMACR: alpha-methylacyl-CoA racemase, AR: androgen receptor, GAPDH: Glyceraldehyde 3-phosphate dehydrogenase; K18: keratin K18.
Figure 21B:
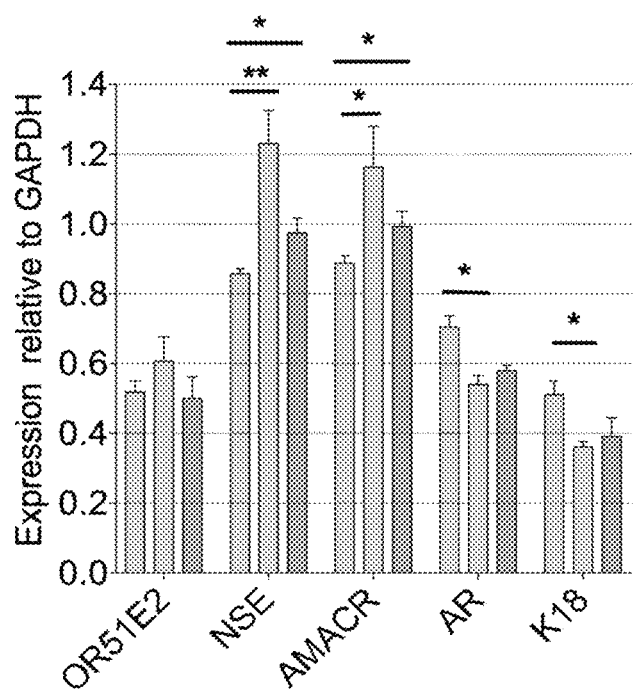
FIG. 21B is a graph of the transcript levels of markers after stimulation with agonists for 12 days, N=3 to 6, unpaired t-test, **P<0.01. *P<0.05
Figure 22A:
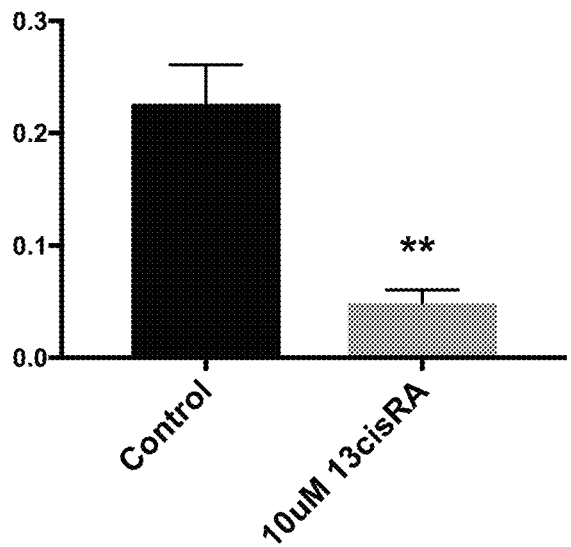
FIG. 22A is a graph showing transcript levels of the OR51E2 gene in cells treated with 13-cis RA as compared to control (untreated) cells.
Figure 22B:
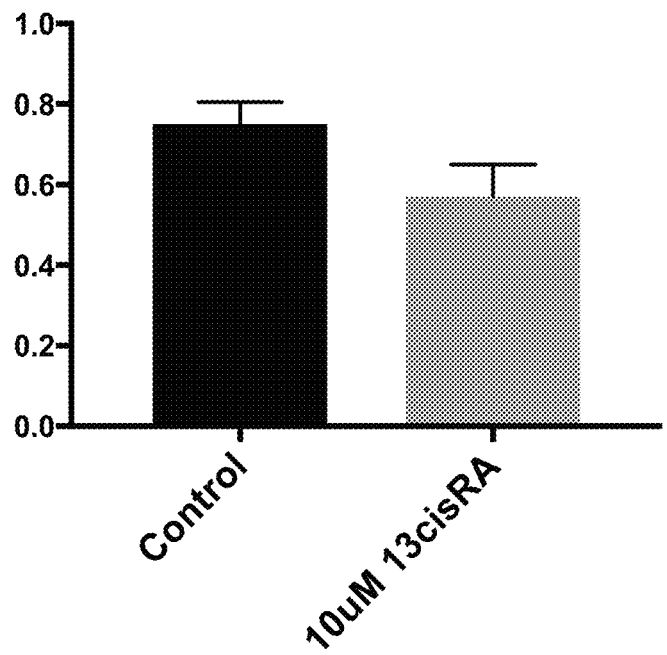
FIG. 22B is a graph showing transcript levels of the NSE gene in cells treated with 13-cis RA as compared to control (untreated) cells.
Figure 23:
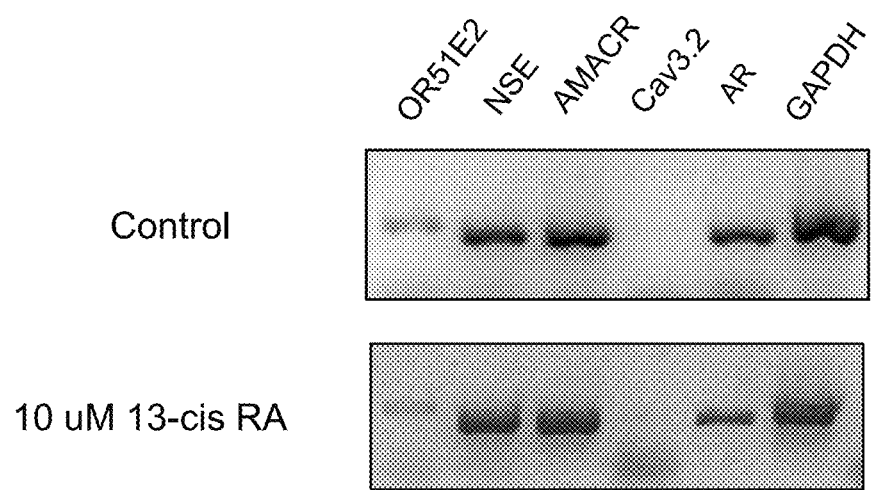
FIG. 23 is a gel showing transcript levels of several genes after 72 hours incubation with 13-cis RA as compared to control by RT-PCR analysis. OR: OR51E2, NSE: neuron specific enolase, AMACR: alpha-methylacyl-CoA racemase, Cav3.2-T-type calcium channel, AR-androgen receptor, GAPDH: Glyceraldehyde 3-phosphate dehydrogenase.

The results indicate that LNCaP cells show alterations in transcript levels of several genes implicated in NEtD after 12 days incubation with the indicated OR51E2 ligands (FIG. 21A and FIG. 21B). For example, 19-OH AD agonist treatment of LNCaP cells increased OR51E2 transcript levels. PA agonist-treatment increased NSE and AMACR transcript levels. Likewise, LNCaP cells treated with 10 μM 13-cisRA for 3 days show significantly decreased OR51E2 transcript levels as compared to control cells (FIG. 22A-22B, FIG. 23). These results are promising and indicate that OR51E2 activation is associated with NEtD. Further studies using siRNA gene knockdown assays, will determine whether activated/overexpressed OR51E2 is involved in NEtD.

LNCaP cells incubated with agonists: 100 nM 19-OH AD, 250 µM AFMK, and 1 mM PA for 72 hours and analyzed with GC/MS (Agilent 6890N GC-5975-Inert MSD) showed significant differences relative to controls (FIG. 24A-24F). GC/MS analysis detected greater than 250 features, and 115 of them were annotated. In FIG. 24A-24F, the top 15 metabolites are presented showing the most significant differences in cells treated with agonists when compared to control cells.

Figure 24A:
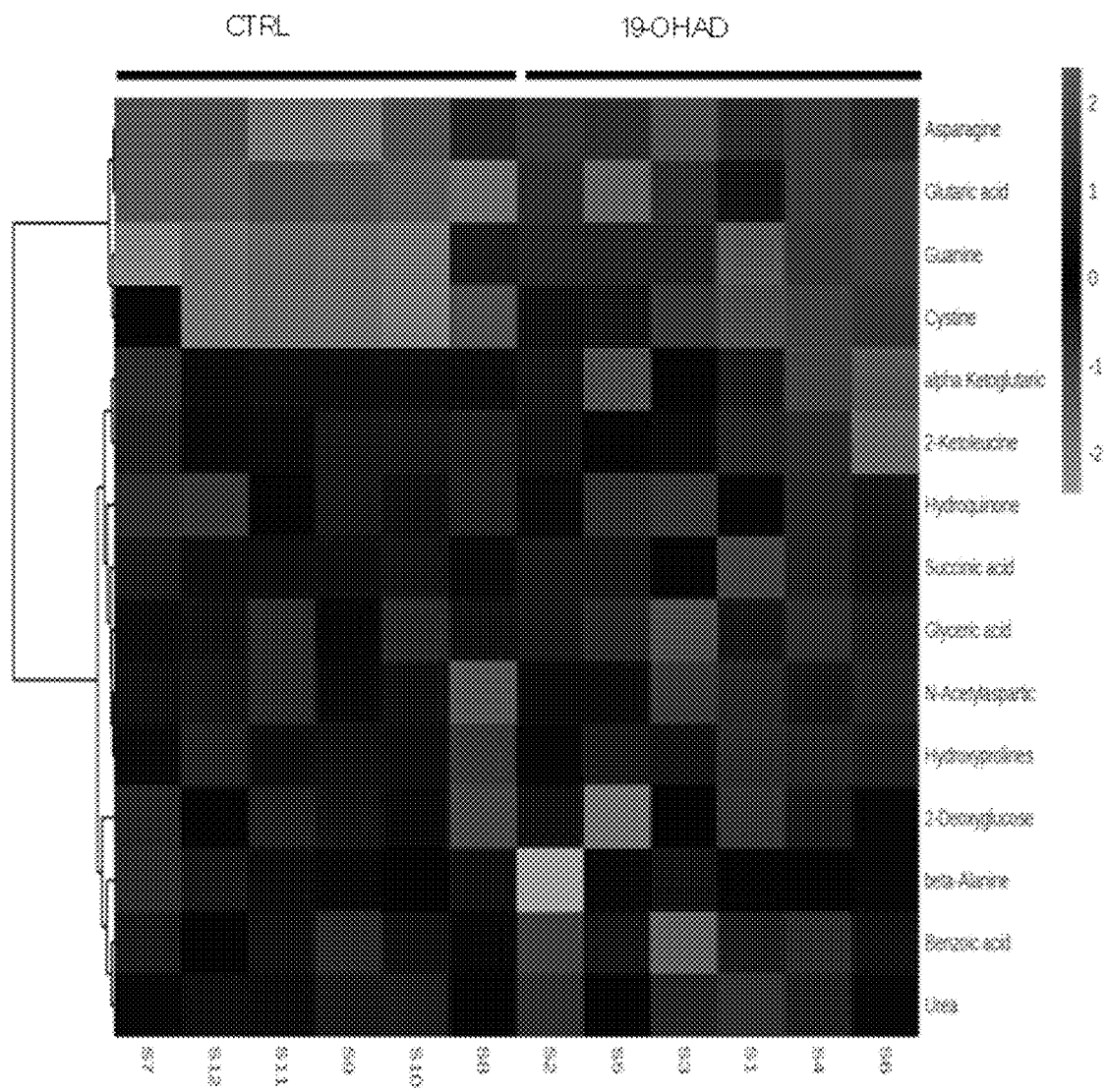
FIG. 24A-24F shows heatmaps of the top 15 extracellular and intracellular metabolites identified after stimulation with 19-OH AD, AFMK, and PA for 72 hours. The top 15 extracellular metabolites identified after stimulation with 19-OH AD (FIG. 24A), AFMK (FIG. 24B), and PA (FIG. 24C). The top 15 intracellular metabolites identified after stimulation with 19-OH AD (FIG. 24D), AFMK (FIG. 24E), and PA (FIG. 24F). Heatmaps are based on the Pearson correlation analysis (Ward) and indicate annotated metabolites identified by t-test ($P<0.05$, $FDR<0.1$, $n=6$). Columns correspond to the samples treated with agonists (S1-6) and control (S7-12), and rows correspond to annotated metabolites. Control samples ($n=6$ biological replicates, t-test, $P<0.05$, MetaboAnalyst 3.0 software).

The top 15 extracellular metabolites identified after stimulation with 19-OH AD were asparagine, glutaric acid, guanine, cysteine, alpha ketoglutaric, 2-ketoleucine, hydroquinone, succinic acid, glyceric acid, n-acetylaspartic, hydroxyprolines, 2-deoxyglucose, beta-alanine, benzoic acid, and urea (FIG. 24A).

Figure 24B:
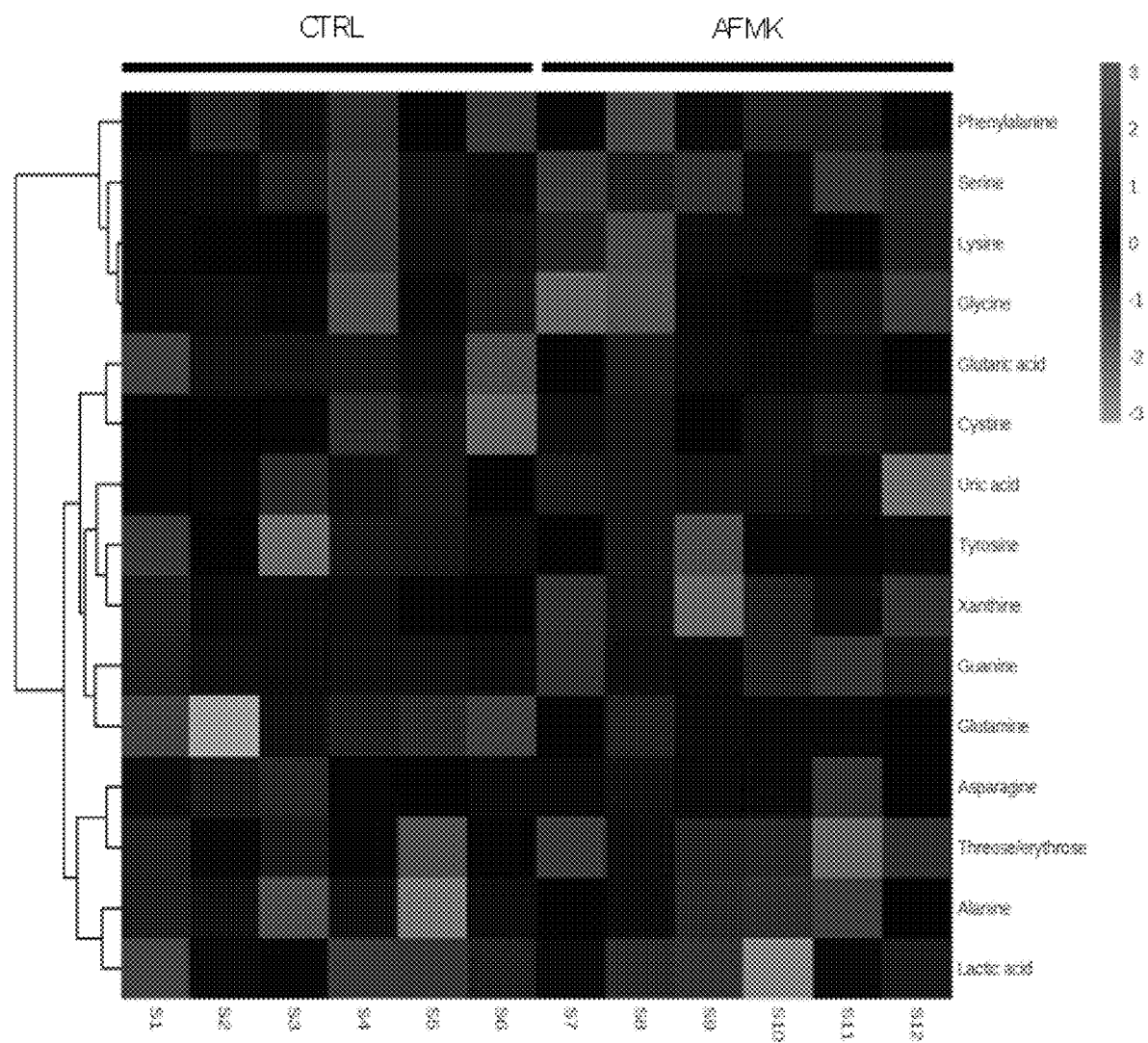

The top 15 extracellular metabolites identified after stimulation with AFMK were phenylalanine, serine, lysine, glycine, glutaric acid, cystine, uric acid, tyrosine, xanthine, guanine, glutamine, asparagine, threose/erythrose, alanine, and lactic acid (FIG. 24B).

Figure 24C:
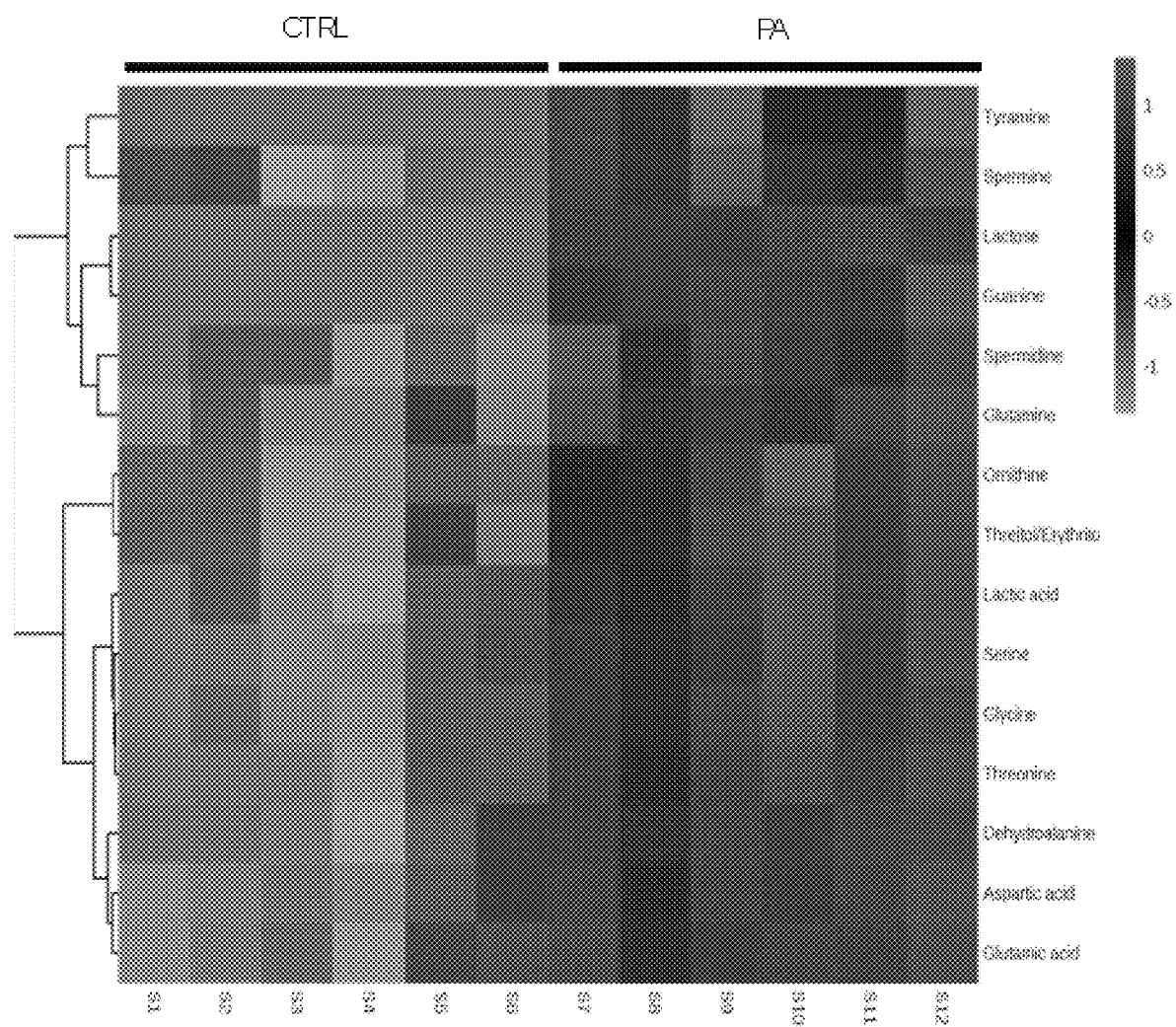

The top 15 extracellular metabolites identified after stimulation with PA were tyramine, spermine, lactose, guanine, spermidine, glutamine, ornithine, threitol/erythritol, lactic acid, serine, glycine, threonine, dehydroalanine, aspartic acid, and glutamic acid (FIG. 24C).

Figure 24D:
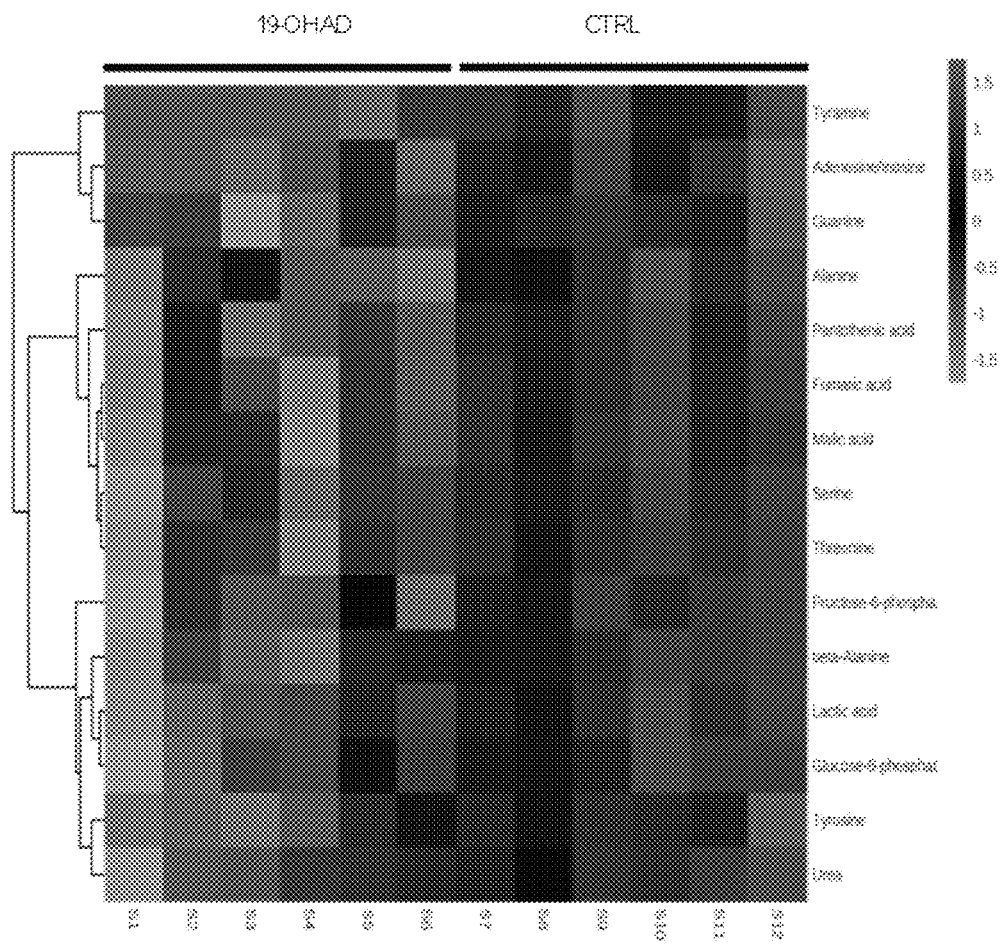

The top 15 intracellular metabolites identified after stimulation with 19-OH AD were tyramine, adenosine/inosine, guanine, alanine, pantothenic acid, fumaric acid, malic acid, serine, threonine, fructose-6-phosphate, beta-alanine, lactic acid, glucose-6-phosphate, tyrosine, and urea (FIG. 24D).

Figure 24E:
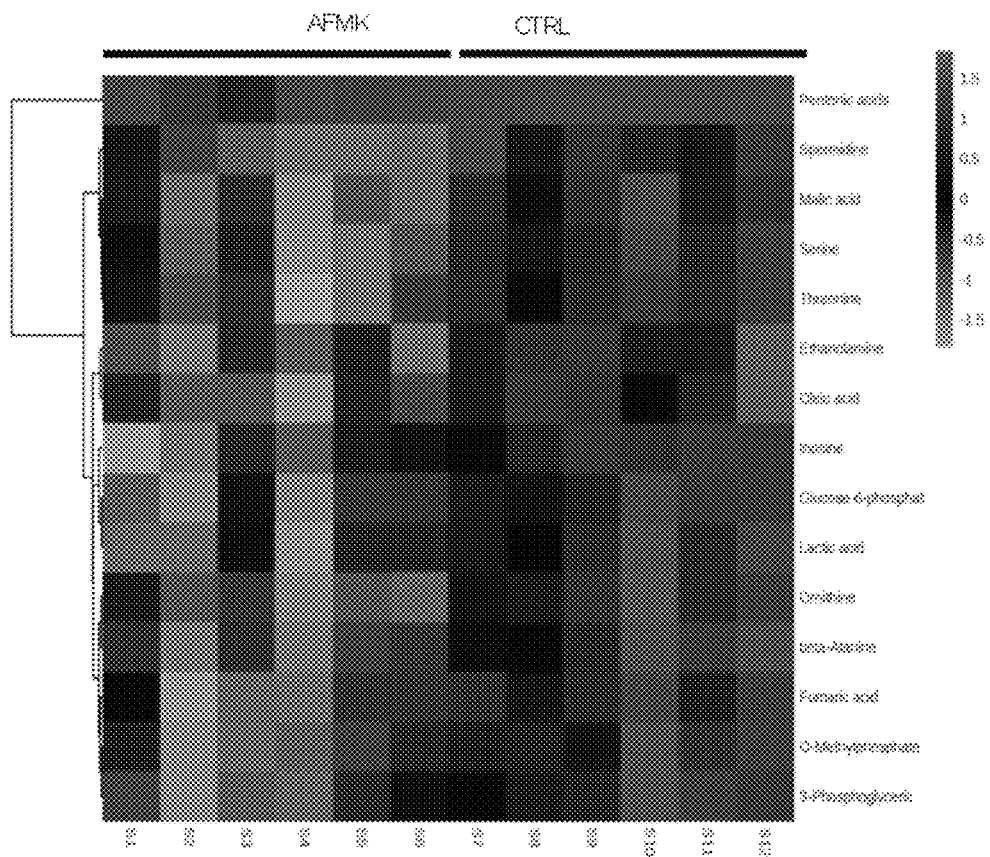

The top 15 intracellular metabolites identified after stimulation with AFMK were pentonic acids, spermidine, malic acid, serine, threonine, ethanolamine, oleic acid, inosine, glucose-6-phosphate, lactic acid, ornithine, beta-alanine, fumaric acid, O-methylphosphate, and 3-phosphoglyceric (FIG. 24E).

Figure 24F:
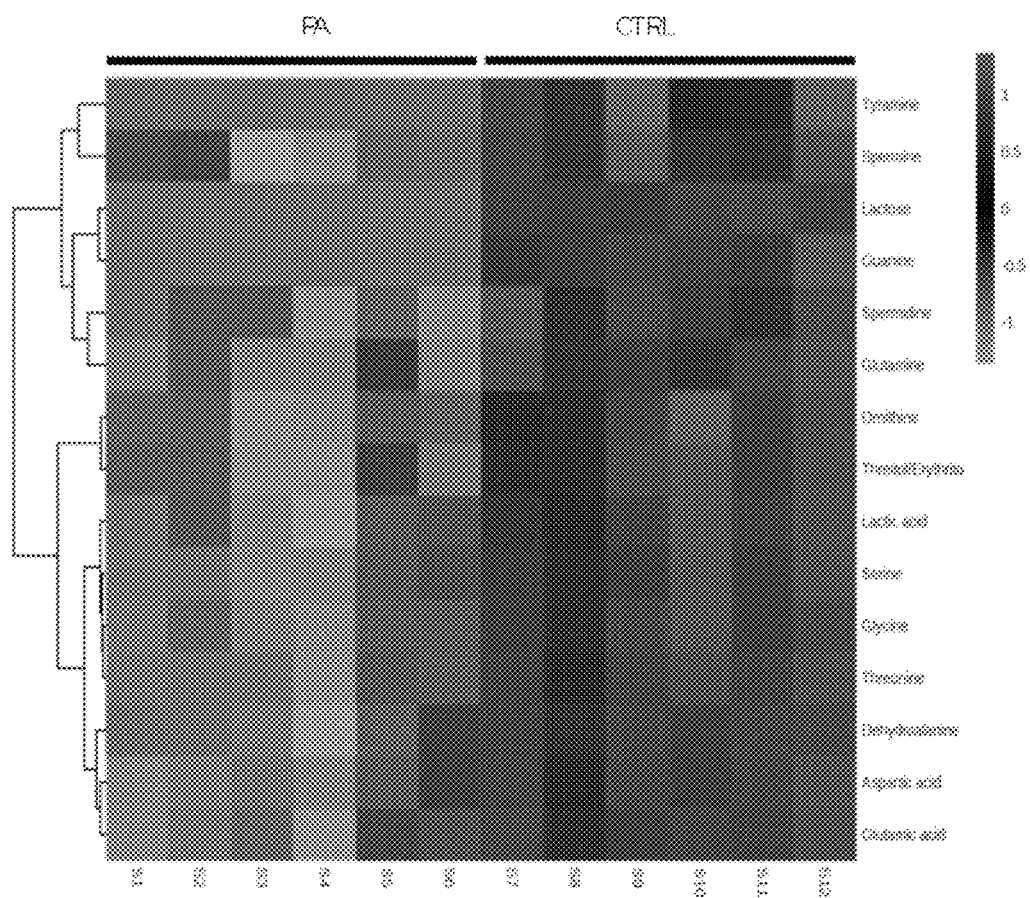
Figure 25A:
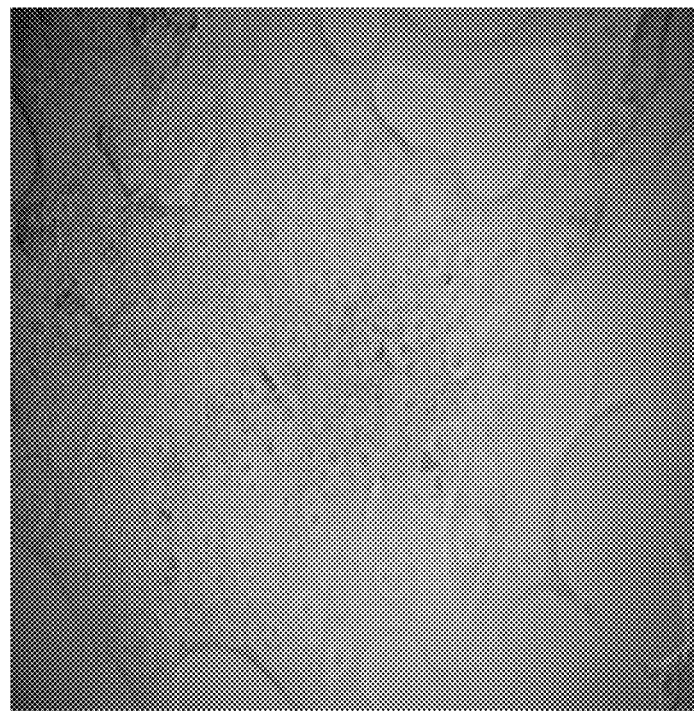
FIG. 25A shows a microscope image of prostate cancer cells growing in regular medium have no NED, shown by absence of neurosecretory granules.
Figure 25B:
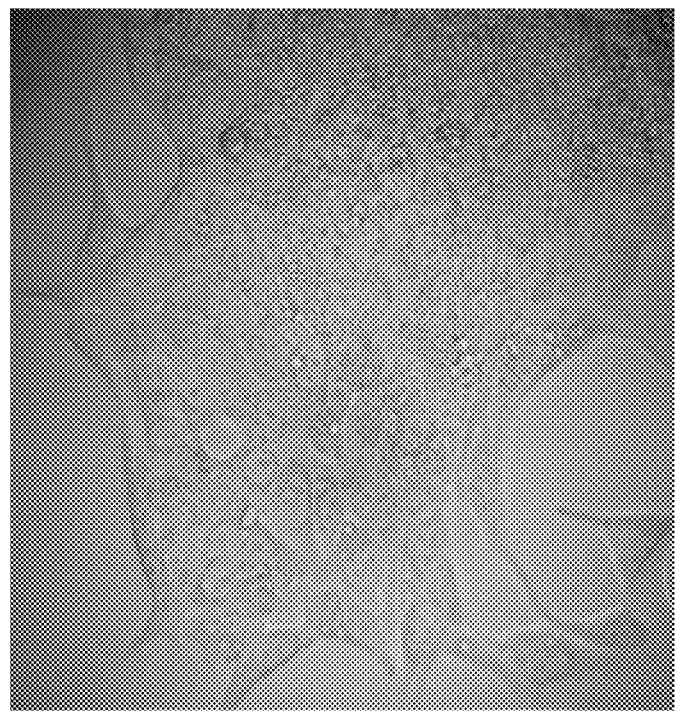
FIG. 25B shows a microscope image of prostate cancer cells growing in androgen depleted medium, which show neurosecretory granules, a sign of NED.
Figure 26A:
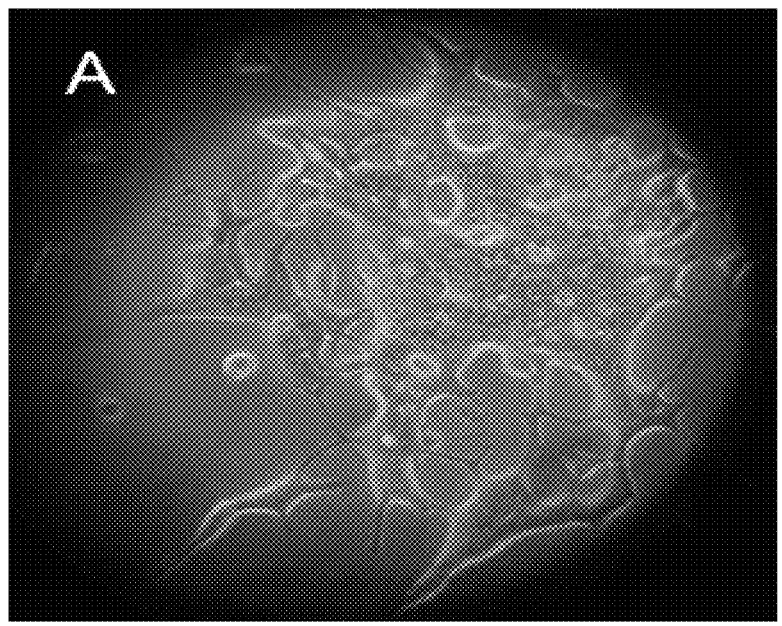
FIG. 26A-26B shows microscope images of the secretory phenotype of LNCaP cells indicative of NED.
Figure 26B:
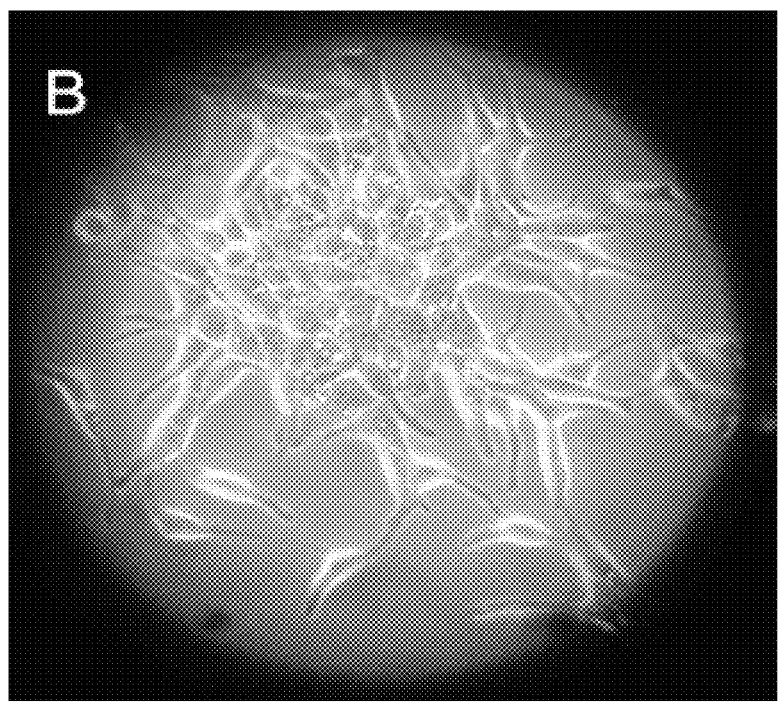

The top 15 intracellular metabolites identified after stimulation with PA were tyramine, spermine, lactose, guanine, spermidine, glutamine, ornithine, threitol/erythritol, lactic acid, serine, glycine, threonine, dehydroalanine, aspartic acid, and glutamic acid (FIG. 24F).

Metabolomics signatures of prostate cancer cells include a decrease in the level of lactic acid, serine, threonine, glucose-6 phosphate, fructose-6 phosphate, fumaric acid, glutamic acid, beta-alanine, ornithine, and inosine. The presence of NEtD of prostate cancer cells can be indicated by a decrease in the intracellular level of the above-mentioned metabolites (FIG. 24D, FIG. 24E and FIG. 24F), and an increase in intracellular phoshoenol-pyruvate, and an increase in extracellular levels of cystine, aparagine, glutaric acid, guanine, glutamine (FIG. 24A, FIG. 24B and FIG. 24C) following treatment with an agonist as compared to prostate cancer cells that were untreated (FIG. 24).

These results also demonstrate that agonist treatment significantly decreased levels of serine and threonine. Because metabolism of these amino acids includes one-carbon metabolism, which provides cofactors for biosynthetic reactions in highly proliferating cells, intracellular depletion may indicate a general decrease in anabolic reactions in agonist-stimulated cells. Furthermore, lactic acid was also decreased, which is in agreement with the attenuated proliferation rate characteristic for NE-like cells. Neuhaus et al. reported that OR51E2/PSGR activation by beta ionone decreased proliferation of LNCaP cells. (Neuhaus et al. (2009) *Journal of Biological Chemistry*, 284:16218-25).

LNCaP cells incubated in androgen-deprived medium (charcoal-dextran treated medium) for five days (n=3, two tailed t-test) show the characteristic NE-like secretory phenotype as compared to those incubated in regulate medium (FIG. 25A-25B and FIG. 26A-26B) and have decreased levels of serine and threonine, indicating that decreases in these amino acids may constitute part of the characteristic NED metabolic profile (Table 2).

TABLE 2

Significantly decreased metabolites identified in LNCaP cell lysates incubated in androgen-deprived medium

| Metabolite | t-test |
|---|---|
| Serine | 0.00005 |
| Threonine | 0.00007 |
| Creatinine | 0.0001 |
| Fructose | 0.0001 |
| Isoleucine | 0.001 |
| Myoinositol | 0.003 |
| Malic acid | 0.007 |
| Glycerol 1-phosphate | 0.011 |
| Hydroxyprolines | 0.015 |
| Glucose | 0.016 |
| Aspartic acid | 0.017 |
| Citric acid | 0.023 |
| Valine | 0.024 |
| Lactic acid | 0.030 |

Figure 27:
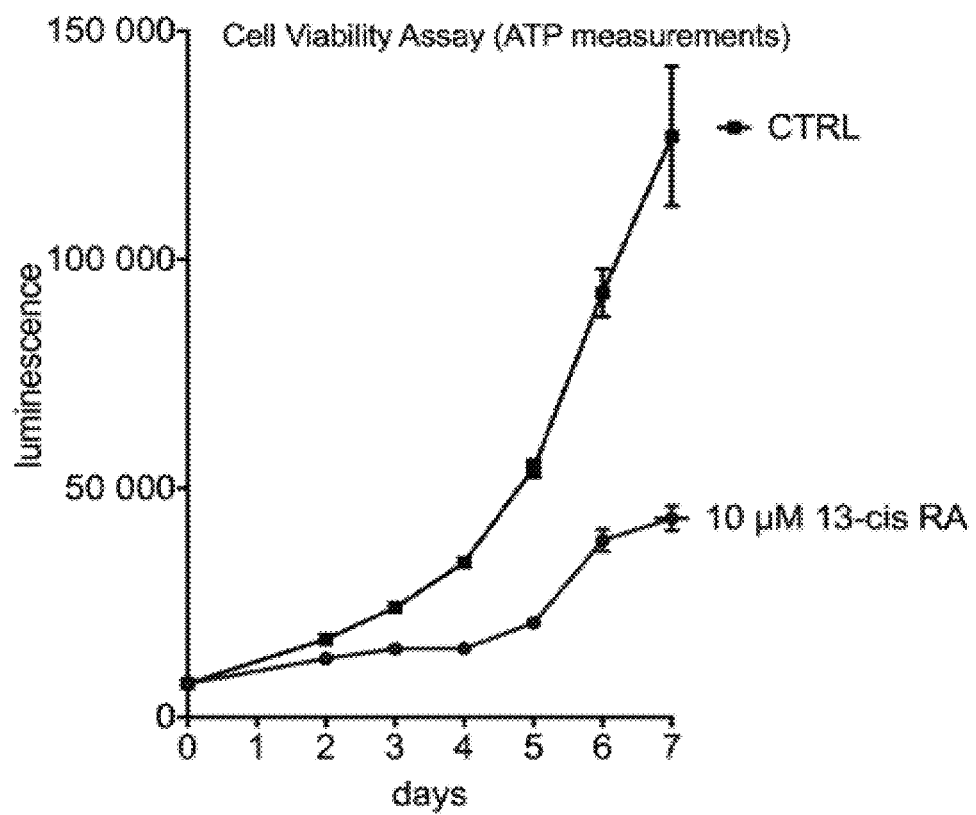
FIG. 27 is a graph of a cell viability/proliferation assay of LNCaP cells treated with 13-cis RA for a 7-day incubation period as compared to control (untreated) cells.

Furthermore, a cell viability/proliferation assay of prostate cancer LNCaP cells was performed using 13-cis RA during a 7 day incubation period. As shown in FIG. 27, 10 uM 13-cis RA effectively impeded LNCaP growth as compared to control (untreated) LNCaP cells.

Discussion

19-OH AD treatment of LNCaP cells increased OR51E2 transcript. PA agonist increased markers of NEtD: NSE and AMACR transcripts. Short term treatment of LNCaP cells with OR51E2 agonists indicate decreased level of several amino-acids. The decreased level of lactate in agonist-treated cells is in agreement with decreased glycolysis characteristic for neuroendocrine cancer phenotype. These results indicate that agonist modulation of OR51E2/PSGR shows changes in cellular metabolism and phenotypic changes indicative of NED. These results point at the OR51E2/PSGR as a valid therapeutic target in designing novel treatment strategies for CRPC.

Figure 28:
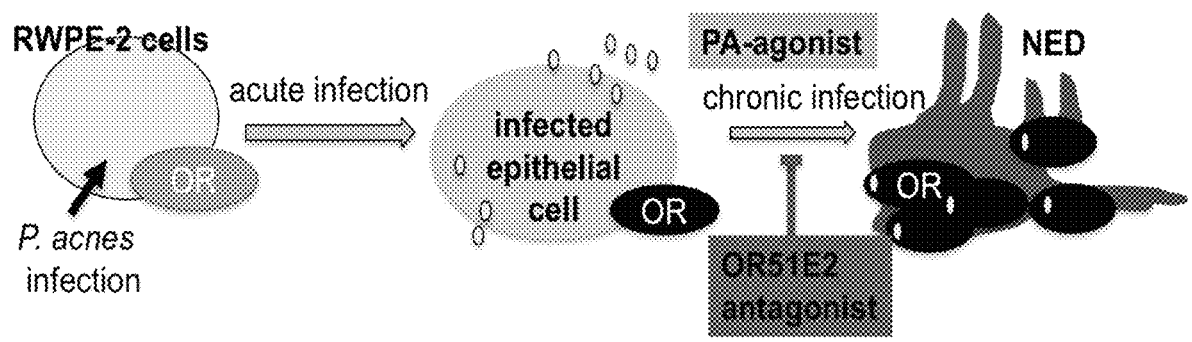
FIG. 28 is a schematic of the assay to study induced NED in prostate epithelial cells via prolonged infection with *P. acnes* with increased secretion of PA.

Example 4: The Ligands for OR51E2/PSGR: A Link Between Prostatic Inflammation and Prostate Cancer To determine if prolonged infection with *P. acnes* with increased secretion of PA can induce NED in prostate epithelial cells, the expression of NED markers (chronic infection) and cytokine secretion (acute infection) will be assessed. The ability of the OR51E2 antagonist to modify and reverse NEtD will also be assessed (FIG. 28).

RWPE-2 cells will be infected with *P. acnes* (ATCC [Manassas, VA] or National Collection of Type Cultures [NCTC, Colindale, London, UK]) using a slightly modified protocol and with the addition of 15% glycerol. Six biological replicates will be performed for each experimental condition. Acute and chronic-prolonged effects will be analyzed at 24 hours and 12 weeks post-infection. In order to sustain prolonged infection, successive infections will be performed every three weeks.

RWPE-2 cells will be incubated with 1 mM PA for 24 hours and 12 weeks, and cytokine release (after 24 hours) and metabolomics signatures (after 12 weeks) will be measured as described above in Example 3. Cytokine release will be measured in RWPE-2 conditioned medium 24 hours post infection using a 40-plex panel kit ELISA assay (Bio-Rad). Metabolomics signatures will be analyzed in both cell lysates and conditioned medium 12 weeks post-infection using an untargeted metabolomics approach. Statistical and enrichment pathway analysis will be done using MetaboAnalyst software.

Antagonist-treated, P. acnes-infected cells will be analyzed for their metabolomics signatures. At three weeks post-infection, antagonist will be added to the medium and the cells will be incubated for the following three weeks. Metabolomics signatures from the treatment and control groups will then be compared using the approach described in Example 3.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods described herein are presently representative of preferred embodiments, are exemplary, and are not intended as limitations on the scope of the invention. Changes therein and other uses will occur to those skilled in the art which are encompassed within the spirit of the invention as defined by the scope of the claims.

The invention claimed is:

1. A method of diagnosing neuroendocrine trans-differentiation of prostate cancer in a subject, the method comprising:
   i) obtaining a biological sample from the subject, wherein the biological sample comprises prostate cancer cells, wherein the prostate cancer cells express OR51E2;
   ii) contacting the sample with one or more OR51E2 ligands, wherein the one or more OR51E2 ligands are 19-hydroxyandrost-4-ene-3,17-dione (19-OH AD), N-acetyl-N-formyl-5-metoxykynurenamine (AFMK), propionic acid (PA), or any combination thereof;
   iii) detecting decreases in the levels of metabolites in the sample from step ii) after contacting the sample with one or more OR51E2 ligands as compared to a control sample, wherein the more metabolites comprise lactic acid, serine, threonine, glucose-6 phosphate, fructose-6 phosphate, fumaric acid, glutamic acid, beta-alanine, ornithine, and inosine;
   iv) detecting increases in the levels of compounds in the sample from step ii) after contacting the sample with one or more OR51E2 ligands as compared to a control sample, wherein the compounds comprise phosphoenolpyruvate, cysteine, asparagine, glutaric acid, guanine, and glutamine; and
   v) identifying the presence of neuroendocrine trans-differentiation of prostate cancer in a subject based on the decreases in the levels of the metabolites and the increases in the levels of the compounds.

2. The method of claim 1, wherein the presence of castrate-resistant prostate cancer is identified.

3. The method of claim 1, wherein the presence of neuroendocrine trans-differentiation of prostate cancer cells is identified.

4. The method of claim 1, wherein the one or more OR51E2 ligand of step ii) comprises 19-OH.

5. The method of claim 1, wherein the one or more OR51E2 ligand of step ii) comprises AFMK.

6. The method of claim 1, wherein the one or more OR51E2 ligand of step ii) comprises PA.

* * * * *